(12) United States Patent
Zhang et al.

(10) Patent No.: US 8,217,051 B2
(45) Date of Patent: Jul. 10, 2012

(54) SPIROINDOLINONE DERIVATIVES

(75) Inventors: Jing Zhang, Parsippany, NJ (US);
Zhuming Zhang, Hillsborough, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 378 days.

(21) Appl. No.: 12/683,468

(22) Filed: Jan. 7, 2010

(65) Prior Publication Data

US 2010/0210674 A1 Aug. 19, 2010

Related U.S. Application Data

(60) Provisional application No. 61/153,089, filed on Feb. 17, 2009.

(51) Int. Cl.
*A61K 31/438* (2006.01)
*A61P 35/00* (2006.01)
*C07D 471/10* (2006.01)
*C07D 209/04* (2006.01)
*C07D 209/54* (2006.01)
*A61K 31/404* (2006.01)

(52) U.S. Cl. .......... 514/278; 546/17; 514/409; 514/418; 548/409; 548/484

(58) Field of Classification Search .................. 514/278, 514/409, 418; 546/17; 548/409, 484
See application file for complete search history.

(56) References Cited

U.S. PATENT DOCUMENTS

| | | | |
|---|---|---|---|
| 7,495,007 B2 * | 2/2009 | Chen et al. | ................... 514/278 |
| 7,553,833 B2 | 6/2009 | Liu et al. | |
| 7,638,548 B2 | 12/2009 | Liu et al. | |
| 2007/0213341 A1 | 9/2007 | Chen et al. | |
| 2008/0009486 A1 | 1/2008 | Chen et al. | |
| 2008/0114013 A1 | 5/2008 | Liu et al. | |
| 2008/0287421 A1 | 11/2008 | Liu et al. | |

FOREIGN PATENT DOCUMENTS

| | | |
|---|---|---|
| EP | 0288847 | 4/1988 |
| EP | 0 947 511 A1 | 10/1999 |
| WO | 01/05790 | 1/2001 |
| WO | 2006091646 | 8/2006 |
| WO | 2007104664 | 9/2007 |
| WO | 2007104714 | 9/2007 |
| WO | 2008/055812 | 5/2008 |
| WO | 2008080822 | 7/2008 |
| WO | 2008005268 | 10/2008 |
| WO | 2009080488 | 7/2009 |

OTHER PUBLICATIONS

J. Amer. Chem. Soc. (2005) 127 p. 10130.
Howard C. Ansel, Pharmaceutical Dosage Forms and Drug Delivery Systems, 6th Ed. 1995, pp. 196, 456-457.
Ghosez, L., etal Tetrahedron 1995—11021-11042.
Lippa, B. et al Bioorganic & Med. Chem. Letters, 18 (11), 2008—3359-3363.
Ding et al, J. Med. Chem. (2006) 49:3432-3435.

* cited by examiner

*Primary Examiner* — Yong Chu
(74) *Attorney, Agent, or Firm* — George W. Johnston; Patricia S. Rocha-Tramaloni

(57) ABSTRACT

There are provided compounds of the formula

I or a pharmaceutically acceptable salt or ester thereof wherein X, Y, $R_1$, $R_2$ are as herein described.
The compounds have utility as antiproliferative agents, especially, as anticancer agents.

6 Claims, No Drawings

SPIROINDOLINONE DERIVATIVES

PRIORITY TO RELATED APPLICATION(S)

This application claims the benefit of U.S. Provisional Application No. 61/153,089, filed Feb. 17, 2009, which is hereby incorporated by reference in its entirety.

SUMMARY OF THE INVENTION

The present invention relates to analogues of spiroindolinones having the formula

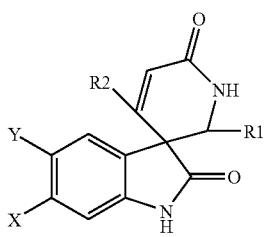

or a pharmaceutically acceptable salt or ester thereof wherein X, Y, $R_1$, $R_2$ are as herein described.
The compounds have utility as antiproliferative agents, especially, as anticancer agents.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

A series of spiroindolinone as antagonists of MDM2 has previously been disclosed in J. Am. Chem. Soc., 2005, 127, 10130 and also in US-2007-0213341-A1 published Sep. 13, 2007.

The present invention provides spiroindolinone derivatives which are small molecule inhibitors of the MDM2-p53 interaction. In cell-free and cell-based assays, compounds of the present invention are shown to inhibit the interaction of MDM2 protein with a p53-like peptide. In cell-based assays, these compounds demonstrate mechanistic activity. Incubation of cancer cells with wild-type p53 leads to accumulation of p53 protein, induction of p53-regulated p21 gene, and cell cycle arrest in G1 and G2 phase, resulting in potent antiproliferative activity against wild-type p53 cells in vitro. In contrast, these activities were not observed in cancer cells with mutant p53 at comparable compound concentrations. Therefore, the activity of MDM2 antagonists is likely linked to its mechanism of action. These compounds can be potent and selective anticancer agents.

DETAILED DESCRIPTION OF THE INVENTION

The present invention relates to spiroindolinones of the formula

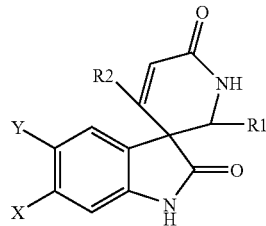

wherein
X is selected from the group consisting of hydrogen, halogen, cyano, nitro, ethynyl, cyclopropyl, methyl, ethyl, isopropyl, methoxy and vinyl,
Y is hydrogen, hydroxyl, or fluorine,
$R_1$ is selected from the group consisting of lower alkenyl, substituted lower alkenyl, aryl, substituted aryl, heteroaryl, substituted heteroaryl, cycloalkenyl and substituted cycloalkenyl and
$R_2$ is selected from the group consisting of aryl, substituted aryl, heteroaryl, substituted heteroaryl, heterocycle, substituted heterocycle, cycloalkenyl and substituted cycloalkenyl or a pharmaceutically acceptable salt or ester thereof.
Preferred are compounds of formula I having a stereochemical structure as shown as formula II

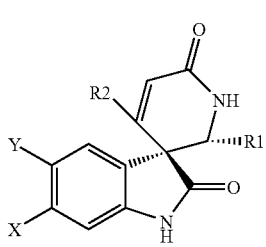

wherein
X is selected from the group consisting of hydrogen, halogen, cyano, nitro, ethynyl, cyclopropyl, methyl, ethyl, isopropyl, methoxy, and vinyl,
Y is hydrogen, hydroxyl, or fluorine, $R_1$ is selected from the group consisting of lower alkenyl, substituted lower alkenyl, aryl, substituted aryl, heteroaryl, substituted heteroaryl, cycloalkenyl and substituted cycloalkenyl and $R_2$ is selected from the group consisting of aryl, substituted aryl, heteroaryl, substituted heteroaryl, heterocycle, substituted heterocycle, cycloalkenyl and substituted cycloalkenyl or a pharmaceutically acceptable salt or ester thereof.

Further preferred are compounds of formula II wherein
X is Cl, F or Br
Y is hydrogen,
$R_2$ is a substituted phenyl or substituted heteroaryl with the substituted phenyl or substituted heteroaryl selected from group consisting of:

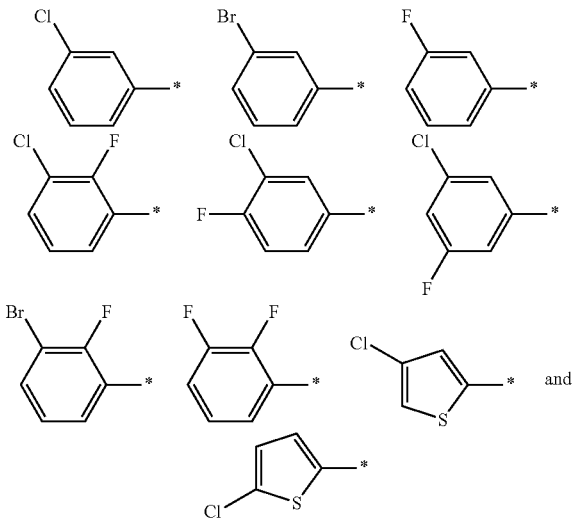

and
$R_1$ is selected from the group consisting of lower alkenyl, substituted lower alkenyl, aryl, substituted aryl, heteroaryl, substituted heteroaryl, cycloalkenyl and substituted cycloalkenyl or a pharmaceutically acceptable salt or ester thereof.

Most preferred compounds are those of the formula:
racemic(2'R,3R)-6-chloro-4'-(3-chloro-phenyl)-2'-(5-fluoro-2-methyl-phenyl)-1',3'-dihydrospiro[3H-indole-3,3'(2'H)-pyridine]-2,6'(1H)-dione;
chiral(2'R,3R)-6-chloro-4'-(3-chloro-phenyl)-2'-(5-fluoro-2-methyl-phenyl)-1',3'-dihydrospiro[3H-indole-3,3'(2'H)-pyridine]-2,6'(1H)-dione;
racemic(2'R,3R)-6-chloro-4'-(3-chloro-phenyl)-2'-(5-fluoro-2-methyl-phenyl)-5-hydroxy-1',3'-dihydrospiro[3H-indole-3,3'(2'H)-pyridine]-2,6'(1H)-dione;
racemic(2'R,3R)-6-chloro-4'-(3-chloro-phenyl)-2'-[5-chloro-2-(tetrahydro-pyran-4-yloxy)-phenyl]-1',3'-dihydrospiro[3H-indole-3,3'-pyridine]-2,6'(1H)-dione;
racemic(2'R,3R)-6-chloro-2'-[5-chloro-2-(tetrahydro-pyran-4-yloxy)-phenyl]-4'-(3-fluoro-phenyl)-1',3'-dihydrospiro[3H-indole-3,3'-pyridine]-2,6'(1H)-dione;
racemic(2'R,3R)-6-chloro-2'-[5-chloro-2-(2-hydroxy-ethoxy)-phenyl]-4'-(5-fluoro-2-methyl-phenyl)-1',3'-dihydrospiro[3H-indole-3,3'-pyridine]-2,6'(1H)-dione;
racemic(2'R,3R)-6-chloro-4'-(3-chloro-phenyl)-2'-isopropenyl-1',3'-dihydrospiro[3H-indole-3,3'-pyridine]-2,6'(1H)-dione;
racemic(2'R,3R)-6-chloro-4'-(3-chloro-phenyl)-5-fluoro-2'-(5-fluoro-2-methyl-phenyl)-1',3'-dihydrospiro[3H-indole-3,3'(2'H)-pyridine]-2,6'(1H)-dione;
racemic(2'R,3R)-6-chloro-2'-(5-fluoro-2-methyl-phenyl)-4'-(furan-3-yl)-1',3'-dihydrospiro[3H-indole-3,3'(2'H)-pyridine]-2,6'(1H)-dione;
racemic(2'R,3R)-6-chloro-2'-(5-fluoro-2-methyl-phenyl)-4'-(thiophen-3-yl)-1',3'-dihydrospiro[3H-indole-3,3'(2'H)-pyridine]-2,6'(1H)-dione;
racemic(2'R,3R)-6-chloro-2'-(5-fluoro-2-methyl-phenyl)-4'-(pyridin-3-yl)-1',3'-dihydrospiro[3H-indole-3,3'(2'H)-pyridine]-2,6'(1H)-dione;
racemic(2'R,3R)-6-chloro-4'-(3-chloro-phenyl)-2'-[5-iodo-2-(tetrahydro-pyran-4-yloxy)-phenyl]-1',3'-dihydrospiro[3H-indole-3,3'-pyridine]-2,6'(1H)-dione;
racemic(2'R,3R)-6-chloro-4'-(3-chloro-phenyl)-2'-[5-ethynyl-2-(tetrahydro-pyran-4-yloxy)-phenyl]-1',3'-dihydrospiro[3H-indole-3,3'-pyridine]-2,6'(1H)-dione;
racemic(2'S,3R)-6-chloro-4'-(3-chloro-phenyl)-2'-[5-ethynyl-2-(tetrahydro-pyran-4-yloxy)-phenyl]-1',3'-dihydrospiro[3H-indole-3,3'-pyridine]-2,6'(1H)-dione;
racemic(2'R,3R)-6-chloro-4'-(5-chloro-furan-2-ylmethylene)-2'-(5-fluoro-2-methyl-phenyl)-1',3'-dihydrospiro[3H-indole-3,3'(2'H)-pyridine]-2,6'(1H)-dione;
racemic(2'R,3R)-6-chloro-4'-(cyclopent-1-enyl)-2'-(5-fluoro-2-methyl-phenyl)-1',3'-dihydrospiro[3H-indole-3,3'(2'H)-pyridine]-2,6'(1H)-dione and
racemic(2'S,3S)-6-chloro-2'-[5-chloro-2-(2-hydroxycarbonyl-1-methyl-ethoxy)-phenyl]-4'-(5-fluoro-2-methyl-phenyl)-1',3'-dihydrospiro[3H-indole-3,3'-pyridine]-2,6'(1H)-dione.

In the specification where indicated the various groups may be substituted by 1-5 or, preferably, 1-3 substituents independently selected from the group consisting of lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxycarbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)-2-lower-alkoxy, benzyloxy-lower-alkoxy, mono- or di-lower alkyl substituted amino-sulfonyl and lower-alkyl which can optionally be substituted with halogen, hydroxy, $NH_2$, N(H, lower-alkyl) or N(lower-alkyl)$_2$. Preferred substituents for the aryl, heteroaryl and heterocycle rings are halogen, lower alkoxy, lower alkyl and amino.

If alkyl, alkenyl, alkynyl or similar groups are linked with both ends to the same moiety, cyclic structures may result, where two hydrogens of said moiety are being replaced by the two ends of the alkyl, alkenyl, alkynyl or similar group, thus creating cyclic structures, such as, tetralin, macrocycles or spiro compounds.

The term "alkyl" refers to straight- or branched-chain saturated hydrocarbon groups having from 1 to about 20 carbon atoms. In certain embodiments, alkyl substituents may be lower alkyl substituents. The term "lower alkyl" refers to alkyl groups having from 1 to 8 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

As used herein, "cycloalkyl" is intended to refer to any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds. Examples of cycloalkenyls include, but are not limited to, cyclopentenyl or cyclohexenyl.

The term "alkenyl" as used herein means an unsaturated straight-chain or branched aliphatic hydrocarbon group containing one double bond and having 2 to 8, preferably 2 to 6 carbon atoms. Examples of such "alkenyl group" are vinyl (ethenyl), allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "halogen" as used in the definitions means fluorine, chlorine, iodine or bromine, preferably fluorine and chlorine.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole and tetrazolyl.

In the case of aryl or heteroaryl which are bicyclic it should be understood that one ring may be aryl while the other is heteroaryl and both being substituted or unsubstituted.

"Heterocycle" means a substituted or unsubstituted 5 to 8 membered, mono- or bicyclic, aromatic or non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like.

"Hetero atom" means an atom selected from N, O and S.

"Alkoxy, alkoxyl or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

The compounds of formula I as well as their salts have at least one asymmetric carbon atom and therefore may be present as racemic mixtures or different stereoisomers. The various isomers can be isolated by known separation methods, e.g., chromatography. The invention includes all stereoisomers.

The compounds of the present invention are useful in the treatment or control of cell proliferative disorders, in particular oncological disorders. These compounds and formulations containing said compounds may be useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I or II or III compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

"Effective amount" means an amount that is effective to prevent, alleviate or ameliorate symptoms of disease or prolong the survival of the subject being treated.

"$IC_{50}$" refers to the concentration of a particular compound required to inhibit 50% of a specific measured activity. $IC_{50}$ can be measured, inter alia, as is described subsequently.

"Pharmaceutically acceptable ester" refers to a conventionally esterified compound of formula I having a carboxyl group or hydroxy group, which esters retain the biological effectiveness and properties of the compound of formula I and are cleaved in vivo (in the organism) to the corresponding active carboxylic acid or alcohol respectively.

Synthesis

Compounds of this invention in formula I or II can be synthesized according to the following general schemes. It will be readily apparent to those of ordinary skill in the art that compounds in formula I-III can be prepared by substitution of the reagents or agents in the general synthesis routes. The starting materials are either commercially available or can be synthesized by well-established literature methods known to those of ordinary skill in the art. Using purification by chiral chromatography, compounds in formula II can be obtained as an optically pure or enriched enantiomers.

Scheme 1

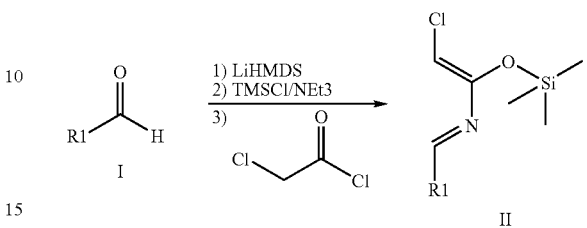

In general an appropriately selected aldehyde I can be reacted with lithium hexamethyldisilamide, chlorotrialkylsilane and a chloroacyl chloride in a one-pot, multi-steps manner to generate 2-aza-1,3-butadiene II (Scheme I) and were used as a crude product. Ghosez, L. and others have reported the preparation of 2-aza-1,3-butadienes and their use in aza Diels-Alder reaction to form heterocycle (Ref: *Tetrahedron* 1995, 11021; *J. Am. Chem. Soc.* 1999, 2617; and literatures cited there). The appropriately selected aldehyde I are either commercially available or can be synthesized by well-established multiple literature methods.

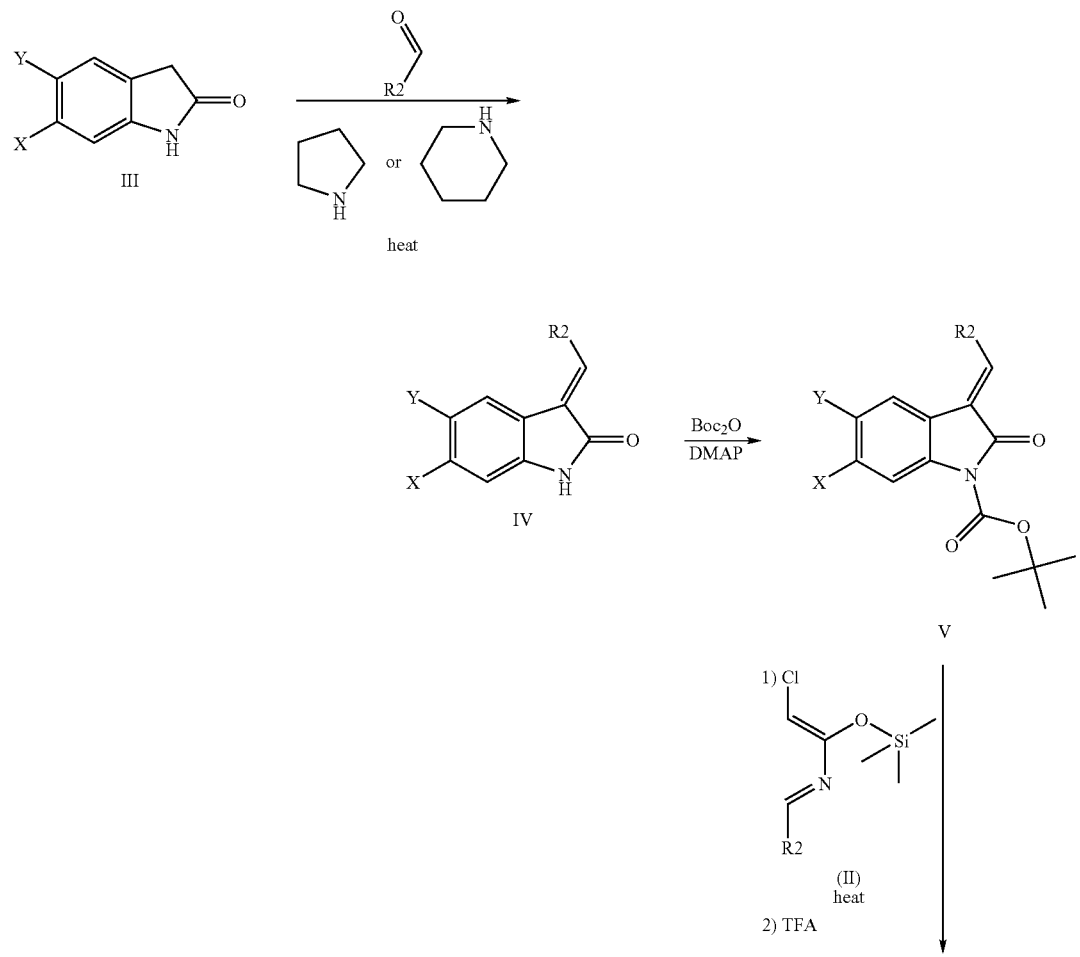

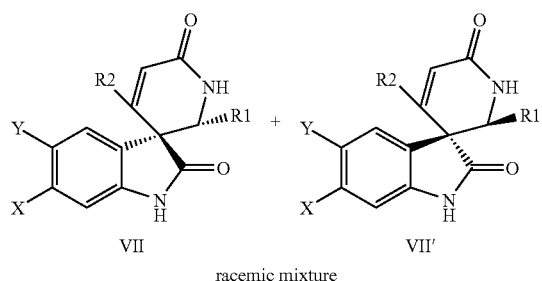

VII racemic mixture

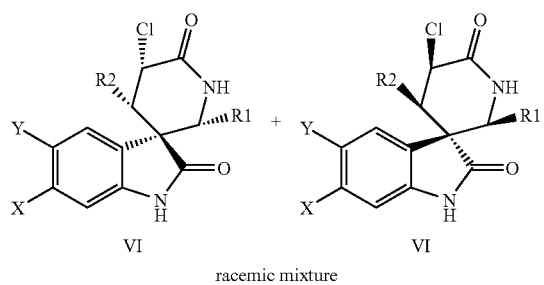

VI racemic mixture 6-substituted or 5,6-disubstituted oxindole III starting materials are either commercially available or prepared according to literature methods, for examples, from the corresponding 4-substituted 2-nitro-fluoro or chlorobenzene according to Kraynack, E. A.; Dalgard, J. E.; Gaeta, F. C. A. *Tetrahedron Letters*, 1998, 39, 7679-7682, or EP153818 for 5-fluoro-6-chlorooxindole. Oxindole III can be reacted with an appropriately substituted aldehyde in the presence of base under heated condition in either a protic solvent to give intermediate IV. The commonly used base is either pyrrolidine or piperidine. Intermediate IV can be converted to intermediate V via a protection reaction using di-tert-butyl dicarbonate and 4-dimethylpyridine or 4-dimethylpyridine and triethylamine combines as the base(s). Intermediate V can then be reacted with 2-aza-1,3-butadiene II in toluene or xylene under heating from 110° C. to 160° C. and anhydrous condition followed by treatment with trifluoroacetic acid in dichloromethane at room temperature to afford a racemic mixture of siproindolinone VI and VI'. Finally a racemic mixture of VI and VI' can be reacted with 1,8-diazabicylo[5.4.0]undec-7-ene (DBU) in toluene under heated conditions (110° C.) to afford racemic mixture of VII and VII' (Scheme 2). Compounds VII and VII' can be readily resolved into two chiral enantiomers by chiral Super Fluid Chromatography (SFC) or chiral HPLC or chiral column chromatography separation to give the two chiral enantiomers.

The following examples and references are provided to aid the understanding of the present invention, the true scope of which is set forth in the appended claims.

EXAMPLE 1

Preparation of intermediate E/Z-6-chloro-3-(3-chloro-benzylidene)-1,3-dihydro-indol-2-one

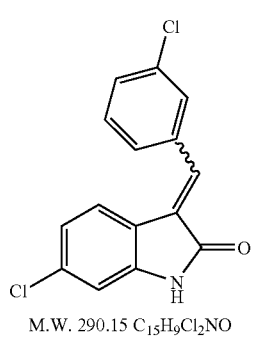

M.W. 290.15 $C_{15}H_9Cl_2NO$

To the mixture of 6-chlorooxindole (16.2 g, 92 mmol) (Crescent) and 3-chloro-benzaldehyde (12.9 g, 92 mmol) (Aldrich) in methanol (109 mL) was added pyrrolidine (6.55 g, 92 mmol) (Aldrich) dropwise. The mixture was then heated at 70° C. for 3 h. After cooled to 4° C., the mixture was filtered and resulting precipitate was collected, dried to give a mixture of E/Z-6-chloro-3-(3-chloro-benzylidene)-1,3-dihydro-indol-2-one as a bright yellow solid (Yield 25.2 g, 95%).

EXAMPLE 2

Preparation of intermediate E/Z-6-chloro-3-(3-chloro-benzylidene)-2-oxo-2,3-dihydro-indole-1-carboxylic acid tert-butyl ester

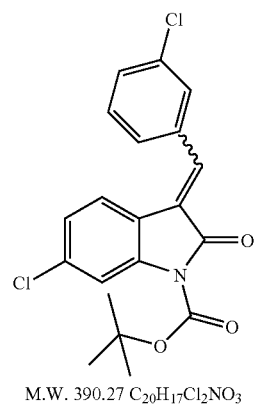

M.W. 390.27 $C_{20}H_{17}Cl_2NO_3$

To a solution of E/Z-6-chloro-3-(3-chloro-benzylidene)-1,3-dihydro-indol-2-one prepared in example 4a (1 g, 3.4 mmol) in dichloromethane (50 mL) at room temperature was added Di-tert-butyl-dicarbonate (1.5 g, 6.9 mmol) (Aldrich), followed by the addition of 4-dimethylaminopyridine (1 g, 8.2 mmol). The reaction mixture was stirred at room temperature for 1 h. The mixture was then concentrated and the residue was purified by chromatography to give E/Z-6-chloro-3-(3-chloro-benzylidene)-2-oxo-2,3-dihydro-indole-1-carboxylic acid tert-butyl ester as an orange solid (Yield 1.3 g, 96%).

EXAMPLE 3

Preparation of intermediate 4-chloro-1-(5-fluoro-2-methyl-phenyl)-3-trimethylsilyoxy-2-aza-1,3-butadiene

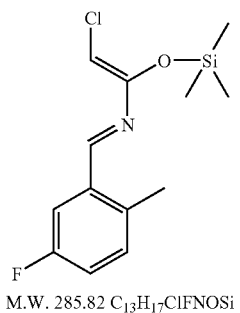

M.W. 285.82 $C_{13}H_{17}ClFNOSi$

To 1,1,1,3,3,3-hexamethyldisilazane (6.54 mL, 31.5 mmol) (Aldrich) under nitrogen at room temperature was added n-butyllithium (2.5 M, 12.6 mL, 31.5 mmol) (Aldrich). The reaction mixture was stirred at room temperature for 10 minutes. Then dry tetrahydrofuran (50 mL) was added, followed by the addition of 5-fluoro-2-methyl-benzaldehyde (4.35 g, 10.5 mmol) (Platte). After the mixture was stirred at room temperature for 0.5 h, trimethylsilyl chloride (4.11 mL, 31.5 mmol) (Aldrich) was added dropwise. Then the temperature of the mixture was lowered to 0° C. on a cooling ice bath. To this mixture was added triethylamine (5.86 mL, 41 mmol) in one portion, followed by the dropwise addition of a solution of chloroacetyl chloride (3.35 mL, 41 mmol) (Aldrich) in diethyl ether (120 mL). The cooling bath was removed, and the mixture was stirred at room temperature for 1 h. The mixture was quickly filtered on celite under nitrogen, and filtrate was concentrated under reduced pressure to give crude 4-chloro-1-(5-fluoro-2-methyl-phenyl)-3-trimethylsilyoxy-2-aza-1,3-butadiene as a yellow gum and used for the next step without further purification.

EXAMPLE 4

Preparation of intermediate racemic(2'R,3R,4'S,5'S)-5',6-dichloro-4'-(3-chloro-phenyl)-2'-(5-fluoro-2-methyl-phenyl)spiro[3H-indole-3,3'-piperidine]-2,6'(1H)-dione

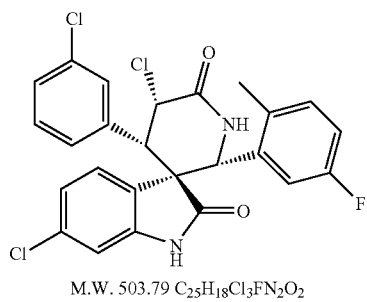

M.W. 503.79 $C_{25}H_{18}Cl_3FN_2O_2$

To a solution of 4-chloro-1-(5-fluoro-2-methyl-phenyl)-3-trimethylsilyoxy-2-aza-1,3-butadiene (31.5 mmol) in toluene (50 mL) was added E/Z-6-chloro-3-(3-chlorobenzylidene)-2-oxo-2,3-dihydro-indole-1-carboxylic acid tert-butyl ester prepared in Example 2 (1.53 g, 3.93 mmol). The reaction mixture was stirred in a sealed tube under nitrogen at 145° C. for 45 min. After the solution was cooled to room temperature, methanol (10 mL) was added. The reaction mixture was filtered through a short pad of celite gel and washed with ethyl acetate. The filtrate was concentrated. The residue was dissolved in dichloromethane (10 mL) and trifluoroacetic acid (10 mL) was added. After the reaction mixture was stirred at room temperature for 1 h, the mixture was concentrated. The residue was partitioned between saturated NaHCO$_3$ solution and ethyl acetate. The aqueous layer was extracted with ethyl acetate. The combined extracts were dried over Na$_2$SO$_4$ and concentrated. The residue was purified by chromatography (EtOAc:hexanes=1; 4, 1:2) to give racemic(2'R,3R,4'S, 5'S)-5',6-dichloro-4'-(3-chloro-phenyl)-2'-(5-fluoro-2-methyl-phenyl)spiro[3H-indole-3,3'-piperidine]-2,6'(1H)-dione as an off-white solid (Yield 0.5 g, 25%).

EXAMPLE 5

Preparation of racemic(2'R,3R)-6-chloro-4'-(3-chloro-phenyl)-2'-(5-fluoro-2-methyl-phenyl)-1',3'-dihydrospiro[3H-indole-3,3'(2'H)-pyridine]-2,6'(1H)-dione

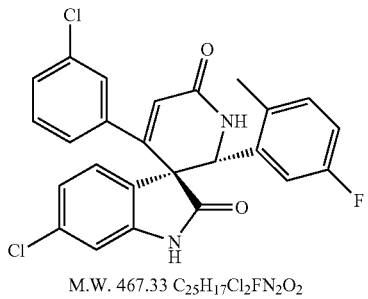

M.W. 467.33 $C_{25}H_{17}Cl_2FN_2O_2$

To a solution of racemic(2'R,3R,4'S, 5'S)-5',6-dichloro-4'-(3-chloro-phenyl)-2'-(5-fluoro-2-methyl-phenyl)spiro[3H-indole-3,3'-piperidine]-2,6'(1H)-dione (0.5 g, 0.99 mmol) in toluene (50 mL) was added 1,8-diazabicyclo[5.4.0]-undec-7-ene (DBU, Aldrich) (1.48 mL, 9.9 mmol). The reaction mixture was heated and stirred at 120° C. for 4 h. After cooled to room temperature, the mixture was concentrated. The residue was partitioned between water solution and ethyl acetate. The aqueous layer was extracted with ethyl acetate. The combined extracts were washed with water, brine, then dried over Na$_2$SO$_4$ and concentrated. The residue was purified by chromatography (EtOAc:hexanes=1; 1, 2:1) to give racemic (2'R, 3R)-6-chloro-4'-(3-chloro-phenyl)-2'-(5-fluoro-2-methyl-phenyl)-1',3'-dihydrospiro[3H-indole-3,3'(2'H)-pyridine]-2, 6'(1H)-dione as an off-white solid (Yield 0.17 g, 37%).

HRMS (ES$^+$) m/z Calcd $C_{25}H_{17}Cl_2FN_2O_2$+H [(M+H)$^+$]: 467.0724. Found: 467.0723.

EXAMPLE 6

Preparation of chiral(2'R,3R)-6-chloro-4'-(3-chloro-phenyl)-2'-(5-fluoro-2-methyl-phenyl)-1',3'-dihydrospiro[3H-indole-3,3'(2'H)-pyridine]-2,6'(1H)-dione

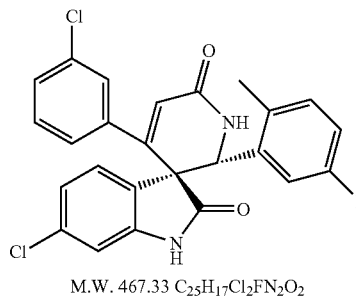

M.W. 467.33 C$_{25}$H$_{17}$Cl$_2$FN$_2$O$_2$

Separation of the two enantiomers from racemic(2'R,3R)-6-chloro-4'-(3-chloro-phenyl)-2'-(5-fluoro-2-methyl-phenyl)-1',3'-dihydrospiro[3H-indole-3,3'(2'H)-pyridine]-2,6'(1H)-dione (90 mg) was conducted by chiral SFC to provide chiral(2'R,3R)-6-chloro-4'-(3-chloro-phenyl)-2'-(5-fluoro-2-methyl-phenyl)-1',3'-dihydrospiro[3H-indole-3,3'(2'H)-pyridine]-2,6'(1H)-dione as an off white solid (28.5 mg, 32%) and chiral(2'S,3S)-6-chloro-4'-(3-chloro-phenyl)-2'-(5-fluoro-2-methyl-phenyl)-1',3'-dihydrospiro[3H-indole-3,3'(2'H)-pyridine]-2,6'(1H)-dione as an off white solid (28.6 mg, 32%).

EXAMPLE 7

Preparation of racemic(2'R,3R)-6-chloro-4'-(3-chloro-phenyl)-2'-(5-fluoro-2-methyl-phenyl)-5-hydroxy-1',3'-dihydrospiro[3H-indole-3,3'(2'H)-pyridine]-2,6'(1H)-dione

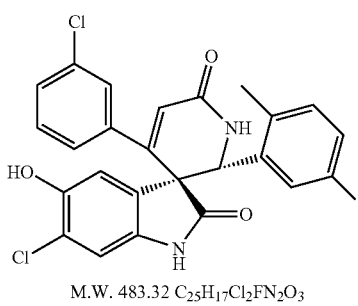

M.W. 483.32 C$_{25}$H$_{17}$Cl$_2$FN$_2$O$_3$

To a solution of racemic(2'R,3R)-6-chloro-4'-(3-chloro-phenyl)-2'-(5-fluoro-2-methyl-phenyl)-1',3'-dihydrospiro[3H-indole-3,3'(2'H)-pyridine]-2,6'(1H)-dione prepared in Example 5 (0.15 g, 0.32 mmol) in methanol (30 mL) was added K$_2$CO$_3$ (0.12 g, 0.87 mmol) and aqueous H$_2$O$_2$ (30%, 2 mL, 0.89 mmol). The reaction mixture was stirred at room temperature for 4 h. Aqueous Na$_2$SO$_3$ solution was added to the reaction mixture, the mixture was then concentrated to a small volume. The mixture was partitioned between water solution and ethyl acetate. The aqueous layer was extracted with ethyl acetate. The combined extracts were washed with water, brine, then dried over Na$_2$SO$_4$ and concentrated to give racemic(2'R,3R)-6-chloro-4'-(3-chloro-phenyl)-2'-(5-fluoro-2-methyl-phenyl)-5-hydroxy-1',3'-dihydrospiro[3H-indole-3,3'(2'H)-pyridine]-2,6'(1H)-dione as a white solid (Yield 0.13 g, 84%).

HRMS (ES$^+$) m/z Calcd C$_{25}$H$_{17}$Cl$_2$FN$_2$O$_3$+H [(M+H)$^+$]: 483.0673. Found: 483.0674

EXAMPLE 8

Preparation of Intermediate Methanesulfonic Acid tetrahydropyran-4-yl ester

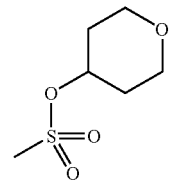

M.W. 180.22 C$_6$H$_{12}$O$_4$S

To a solution of 4-hydroxytetrahydropyran (4.5 g, 44 mmol) (Aldrich) in dichloromethane (90 mL) at 0° C. was added triethylamine (5.4 g, 53 mmol), and methanesulfonyl chloride (3.73 mL, 48 mmol, Aldrich). The reaction mixture was stirred at 0° C. for 1 h, then at room temperature for 1.5 h. The mixture was poured into water, extracted with dichloromethane. The organic layer was separated, washed with water, brine, dried over MgSO$_4$, and concentrated to give crude methanesulfonic acid tetrahydropyran-4-yl ester as a white solid (Yield 8 g, 100%).

Similar transformation has been described by Suto, M. J. et al in *J. Med. Chem.*, 1991, 2484.

EXAMPLE 9

Preparation of intermediate 5-chloro-2-(tetrahydro-pyran-4-yloxy)-benzaldehyde

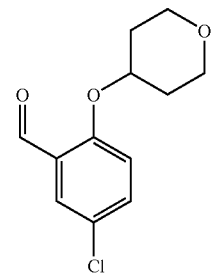

M.W. 240.69 C$_{12}$H$_{13}$ClO$_3$

To a solution of chlorosalicylaldehyde (2.18 g, 13.8 mmol) (Aldrich) in N,N-dimethylformamide (50 mL) was added anhydrous Cs$_2$CO$_3$ (13.58 g, 42 mmol), and 4-(toluene-4-sulfonyloxy)-piperidine-1-carboxylic acid tert-butyl ester (4.5 g, 20.8 mmol). The reaction mixture was heated at 140° C. for 1 h. The mixture was cooled to room temperature, diluted with ethyl acetate, washed with water. The organic layer was separated, the aqueous layer was extracted with ethyl acetate. The organic layers were combined, washed with water, brine, dried over MgSO$_4$, and concentrated to give crude 5-chloro-2-(tetrahydro-pyran-4-yloxy)-benzaldehyde as a yellow solid (Yield 3.2 g, 95%).

EXAMPLE 10

Preparation of intermediate 4-chloro-1-[5-chloro-2-(tetrahydro-pyran-4-yloxy)-phenyl]-3-trimethylsilyoxy-2-aza-1,3-butadiene

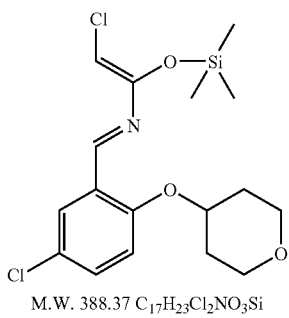

M.W. 388.37 $C_{17}H_{23}Cl_2NO_3Si$

In a manner similar to the method described in Example 3, 5-chloro-2-(tetrahydro-pyran-4-yloxy)-benzaldehyde (1.6 g, 6.44 mmol) was reacted with 1,1,1,3,3,3-hexamethyldisilazane (1.38 mL, 6.44 mmol), n-butyllithium (2.5 M, 2.6 mL, 6.44 mmol), trimethylsilyl chloride (0.85 mL, 6.44 mmol), triethylamine (1.2 mL, 8.37 mmol) and chloroacetyl chloride (0.69 mL, 8.37 mmol) to give crude 4-chloro-1-[5-chloro-4-2-(tetrahydro-pyran-4-yloxy)-phenyl]-3-trimethylsilyoxy-2-aza-1,3-butadiene as a yellow gum and used for the next step without further purification.

EXAMPLE 11

Preparation of Intermediate racemic(2'R,3R,4'S, 5'S)-5',6-dichloro-2'-[5-chloro-2-(tetrahydro-pyran-4-yloxy)-phenyl]-4'-(3-chlorophenyl)spiro[3H-indole-3,3'-piperidine]-2,6'(1H)-dione

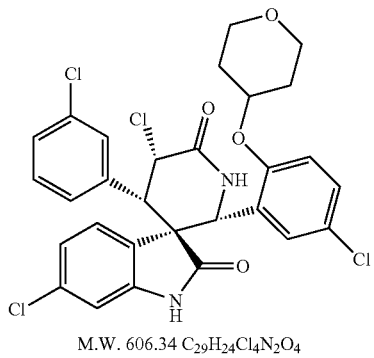

M.W. 606.34 $C_{29}H_{24}Cl_4N_2O_4$

In a manner similar to the method described in Example 4, E/Z-6-chloro-3-(3-chloro-benzylidene)-2-oxo-2,3-dihydro-indole-1-carboxylic acid tert-butyl ester prepared in Example 2 (0.31 g, 0.8 mmol) was reacted with 4-chloro-1-[5-chloro-2-(tetrahydro-pyran-4-yloxy)-phenyl]-3-trimethylsilyoxy-2-aza-1,3-butadiene (6.44 mmol) in toluene, then treated with trifluoroacetic acid in dichloromethane to give racemic(2'R, 3R,4'S, 5'S)-5',6-dichloro-2'-[5-chloro-2-(tetrahydro-pyran-4-yloxy)-phenyl]-4'-(3-chlorophenyl)spiro[3H-indole-3,3'-piperidine]-2,6'(1H)-dione as a yellow solid (Yield 0.25 g, 52%)

EXAMPLE 12

Preparation of racemic(2'R,3R)-6-chloro-4'-(3-chloro-phenyl)-2'-[5-chloro-2-(tetrahydro-pyran-4-yloxy)-phenyl]-1',3'-dihydrospiro[3H-indole-3,3'-pyridine]-2,6'(1H)-dione

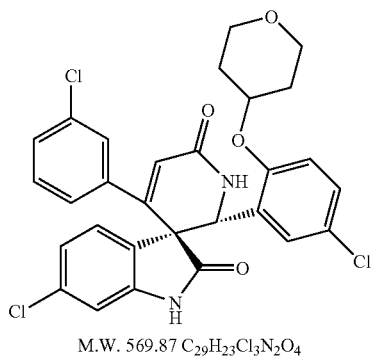

M.W. 569.87 $C_{29}H_{23}Cl_3N_2O_4$

In a manner similar to the method described in Example 5, racemic(2'R,3R,4'S, 5'S)-5',6-dichloro-2'-[5-chloro-2-(tetrahydro-pyran-4-yloxy)-phenyl]-4'-(3-chlorophenyl) spiro [3H-indole-3,3'-piperidine]-2,6'(1H)-dione in Example 10 (0.25 g, 0.41 mmol) was heated with DBU in toluene to give racemic(2'R,3R)-6-chloro-4'-(3-chloro-phenyl)-2'-[5-chloro-2-(tetrahydro-pyran-4-yloxy)-phenyl]-1',3'-dihydrospiro[3H-indole-3,3'-pyridine]-2,6'(1H)-dione as a yellow solid (Yield 25 mg, 11%)

HRMS (ES$^+$) m/z Calcd $C_{29}H_{23}Cl_3N_2O_4$+H [(M+H)$^+$]: 569.0796. Found: 569.0800.

EXAMPLE 13

Preparation of intermediate 6-chloro-3-[1-(3-fluoro-phenyl)-methylidene]-1,3-dihydro-indol-2-one

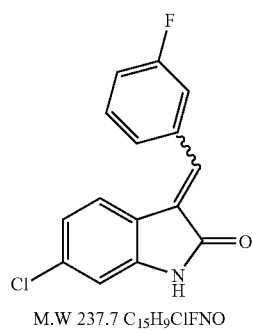

M.W 237.7 $C_{15}H_9ClFNO$

In a manner similar to the method described in Example 1, 6-chlorooxindole (3.61 g, 21.5 mmol) was reacted with 3-fluoro-benzaldehyde (Aldrich, 2.26 mL, 21.5 mmol) and piperidine (2.12 mL, 21.5 mmol) in methanol to give 6-chloro-3-[1-(3-fluoro-phenyl)-methylidene]-1,3-dihydro-indol-2-one as a yellow solid (Yield 4.5 g, 76%).

EXAMPLE 14

Preparation of intermediate E/Z-6-chloro-3-[1-(3-fluoro-phenyl)-methylidene]-2-oxo-2,3-dihydro-indole-1-carboxylic acid tert-butyl ester

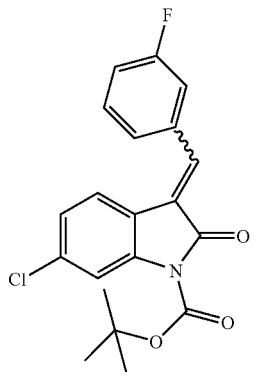

M.W 373.8 C$_{20}$H$_{17}$ClFNO$_3$

In a manner similar to the method described in Example 2, E/Z-6-chloro-3-[1-(3-fluoro-phenyl)-methylidene]-1,3-dihydro-indol-2-one (4.5 g, 16.4 mmol) was reacted with di-tert-butyl-dicarbonate (3.94 g, 18 mmol) and 4-dimethylaminopyridine (80 mg) in dichloromethane to give E/Z-6-chloro-3-[1-(3-fluoro-phenyl)-methylidene]-2-oxo-2,3-dihydro-indole-1-carboxylic acid tert-butyl ester as a yellow solid (Yield 5.8 g, 94%).

EXAMPLE 15

Preparation of Intermediate racemic(2'R,3R,4'S, 5'S)-5',6-dichloro-2'-[5-chloro-2-(tetrahydro-pyran-4-yloxy)-phenyl]-4'-(3-fluoro-phenyl)spiro[3H-indole-3,3'-piperidine]-2,6'(1H)-dione

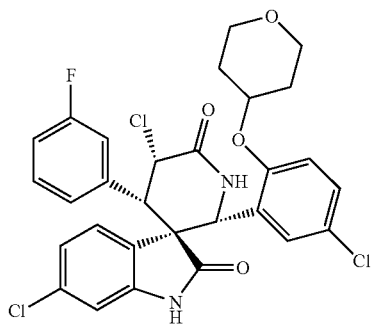

M.W. 589.88 C$_{29}$H$_{24}$Cl$_3$FN$_2$O$_4$

In a manner similar to the method described in Example 4, E/Z-6-chloro-3-[1-(3-fluoro-phenyl)-methylidene]-2-oxo-2,3-dihydro-indole-1-carboxylic acid tert-butyl ester prepared in Example 14 (0.3 g, 0.8 mmol) was reacted with 4-chloro-1-[5-chloro-2-(tetrahydro-pyran-4-yloxy)-phenyl]-3-trimethylsilyoxy-2-aza-1,3-butadiene prepared in Example 10 (6.44 mmol) in toluene, then treated with trifluoroacetic acid in dichloromethane to give racemic(2'R,3R,4'S, 5'S)-5',6-dichloro-2'-[5-chloro-2-(tetrahydro-pyran-4-yloxy)-phenyl]-4'-(3-fluoro-phenyl)spiro[3H-indole-3,3'-piperidine]-2, 6'(1H)-dione as a yellow solid (Yield 0.15 g, 32%)

EXAMPLE 16

Preparation of racemic(2'R,3R)-6-chloro-2'-[5-chloro-2-(tetrahydro-pyran-4-yloxy)-phenyl]-4'-(3-fluoro-phenyl)-1',3'-dihydrospiro[3H-indole-3,3'-pyridine]-2,6'(1H)-dione

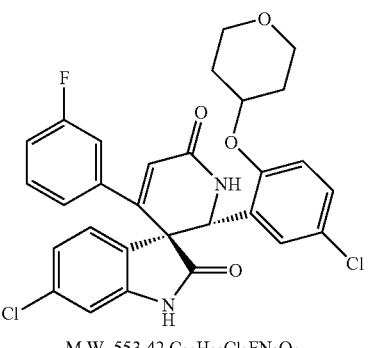

M.W. 553.42 C$_{29}$H$_{23}$Cl$_2$FN$_2$O$_4$

In a manner similar to the method described in Example 5, racemic(2'R,3R,4'S, 5'S)-5',6-dichloro-2'-[5-chloro-2-(tetrahydro-pyran-4-yloxy)-phenyl]-4'-(3-fluoro-phenyl) spiro [3H-indole-3,3'-piperidine]-2,6'(1H)-dione in Example 16 (0.15 g, 0.25 mmol) was heated with DBU in toluene to give racemic(2'R,3R)-6-chloro-2'-[5-chloro-2-(tetrahydro-pyran-4-yloxy)-phenyl]-4'-(3-fluoro-phenyl)-1',3'-dihydrospiro [3H-indole-3,3'-pyridine]-2,6'(1H)-dione as a yellow solid (Yield 50 mg, 36%)

HRMS (ES$^+$) m/z Calcd C$_{29}$H$_{23}$Cl$_2$FN$_2$O$_4$+H [(M+H)$^+$]: 553.1092. Found: 553.1093

EXAMPLE 17

Preparation of intermediate 2-[2-(tert-butyl-dimethyl-silanyloxy)-ethoxy]-5-chloro-benzaldehyde

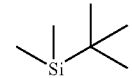
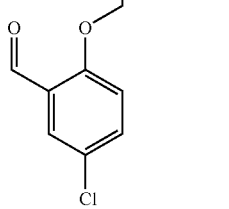

M.W. 314.89 C$_{15}$H$_{23}$ClO$_3$Si

To a solution of 5-chlorosalicylaldehyde (5 g, 32 mmol) (Aldrich) in N,N-dimethylformamide (40 mL) was added K$_2$CO$_3$ (20 g, 145 mmol), and (2-bromo-ethoxy)-tert-butyl-dimethyl-silane (10 g, 42 mmol, Aldrich). The reaction mixture was heated at 60° C. for 18 h. The crude was cooled to room temperature, diluted with ethyl acetate, washed with water, brine. The organic layer was separated, concentrated, and the residue was purified by chromatography (EtOAc:Hexanes=1:8, then 1:4) to give 2-[2-(tert-butyl-dimethyl-silanyloxy)-ethoxy]-5-chloro-benzaldehyde as a white solid (Yield 10 g, 99%).

EXAMPLE 18

Preparation of intermediate E/Z-3-{2-[2-(tert-butyl-dimethyl-silanyloxy)-ethoxy]-5-chloro-benzylidene}-6-chloro-1,3-dihydro-indol-2-one

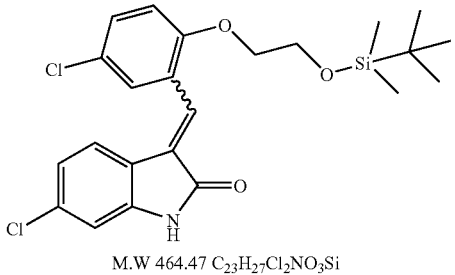

M.W 464.47 $C_{23}H_{27}Cl_2NO_3Si$

In a manner similar to the method described in Example 1, 6-chlorooxindole (2.37 g, 12.7 mmol) was reacted with 2-[2-(tert-butyl-dimethyl-silanyloxy)-ethoxy]-5-chloro-benzaldehyde prepared in Example 18 (4 g, 12.7 mmol) and piperidine (1.25 mL, 12.7 mmol) in methanol to give E/Z-3-{2-[2-(tert-butyl-dimethyl-silanyloxy)-ethoxy]-5-chloro-benzylidene}-6-chloro-1,3-dihydro-indol-2-one as a yellow solid (Yield 5.46 g, 92%).

EXAMPLE 19

Preparation of intermediate E/Z-3-{2-[2-(tert-butyl-dimethyl-silanyloxy)-ethoxy]-5-chloro-benzylidene}-6-chloro-2-oxo-2,3-dihydro-indole-1-carboxylic acid tert-butyl ester

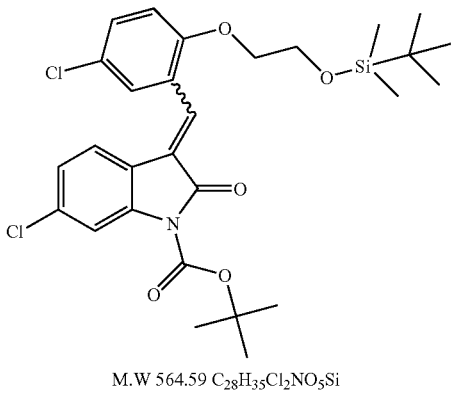

M.W 564.59 $C_{28}H_{35}Cl_2NO_5Si$

In a manner similar to the method described in Example 2, E/Z-3-{2-[2-(tert-butyl-dimethyl-silanyloxy)-ethoxy]-5-chloro-benzylidene}-6-chloro-1,3-dihydro-indol-2-one (5.46 g, 12 mmol) was reacted with di-tert-butyl-dicarbonate (3.33 g, 15.3 mmol), triethylamine (6.54 mL, 47 mmol), and 4-dimethylaminopyridine (57 mg) in dichloromethane to give E/Z-3-{2-[2-(tert-butyl-dimethyl-silanyloxy)-ethoxy]- 5-chloro-benzylidene}-6-chloro-2-oxo-2,3-dihydro-indole-1-carboxylic acid tert-butyl ester as a yellow solid (Yield 4.8 g, 72.7%).

EXAMPLE 20

Preparation of Intermediate racemic(2'R,3R,4'S, 5'S)-5',6-dichloro-4'-[5-chloro-2-(2-hydroxy-ethoxy)-phenyl]-2'-(5-fluoro-2-methyl-phenyl)spiro[3H-indole-3,3'-piperidine]-2,6'(1H)-dione

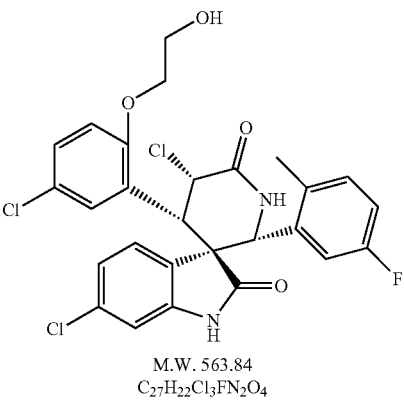

M.W. 563.84
$C_{27}H_{22}Cl_3FN_2O_4$

In a manner similar to the method described in Example 4, E/Z-3-{2-[2-(tert-butyl-dimethyl-silanyloxy)-ethoxy]-5-chloro-benzylidene}-6-chloro-2-oxo-2,3-dihydro-indole-1-carboxylic acid tert-butyl ester prepared in Example 19 (1.48 g, 2.62 mmol) was reacted with 4-chloro-1-(5-fluoro-2-methyl-phenyl)-3-trimethylsilyoxy-2-aza-1,3-butadiene prepared in Example 3 (21 mmol) in toluene, then treated with trifluoroacetic acid in dichloromethane to give racemic(2'R, 3R,4'S, 5'S)-5',6-dichloro-4'-[5-chloro-2-(2-hydroxy-ethoxy)-phenyl]-2'-(5-fluoro-2-methyl-phenyl)spiro[3H-indole-3,3'-piperidine]-2,6'(1H)-dione as a yellow solid (Yield 0.2 g, 14%)

EXAMPLE 21

Preparation of racemic(2'R,3R)-6-chloro-2'-[5-chloro-2-(2-hydroxy-ethoxy)-phenyl]-4'-(5-fluoro-2-methyl-phenyl)-1',3'-dihydrospiro[3H-indole-3,3'-pyridine]-2,6'(1H)-dione

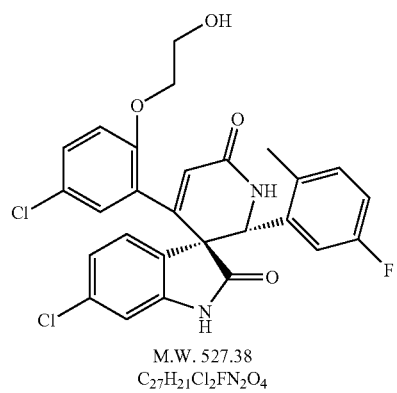

M.W. 527.38
$C_{27}H_{21}Cl_2FN_2O_4$

In a manner similar to the method described in Example 5, racemic(2'R,3R,4'S, 5'S)-5',6-dichloro-4'-[5-chloro-2-(2-hydroxy-ethoxy)-phenyl]-2'-(5-fluoro-2-methyl-phenyl) spiro[3H-indole-3,3'-piperidine]-2,6'(1H)-dione in Example 20 (0.2 g, 0.35 mmol) was heated with DBU in toluene to give racemic(2'R,3R)-6-chloro-2'-[5-chloro-2-(2-hydroxy-ethoxy)-phenyl]-4'-(5-fluoro-2-methyl-phenyl)-1',3'-dihydrospiro[3H-indole-3,3'-pyridine]-2,6'(1H)-dione as a light yellow solid (Yield 30 mg, 16%)

MS (ES$^+$) m/z Calcd $C_{27}H_{21}Cl_2FN_2O_4$+H [(M+H)$^+$]: 527. Found: 527.

EXAMPLE 22

Preparation of intermediate 4-chloro-1-isopropenyl-3-trimethylsilyoxy-2-aza-1,3-butadiene

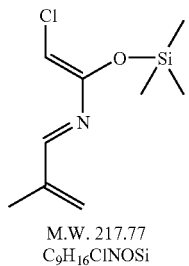

M.W. 217.77
$C_9H_{16}ClNOSi$

In a manner similar to the method described in Example 3, 2-methacrolein (0.81 g, 10.5 mmol) (Acros) was reacted with 1,1,1,3,3,3-hexamethyldisilazane (2.18 mL, 10.5 mmol), n-butyllithium (2.5 M, 4.2 mL, 10.5 mmol), trimethylsilyl chloride (1.33 mL, 10.5 mmol), triethylamine (1.89 mL, 14 mmol) and chloroacetyl chloride (1.09 mL, 14 mmol) to give crude 4-chloro-1-isopropenyl-3-trimethylsilyoxy-2-aza-1,3-butadiene as a yellow gum and used for the next step without further purification.

EXAMPLE 23

Preparation of intermediate racemic(2'R,3R,4'S, 5'S)-5',6-dichloro-4'-(3-chloro-phenyl)-2'-isopropenyl spiro[3H-indole-3,3'-piperidine]-2,6'(1H)-dione

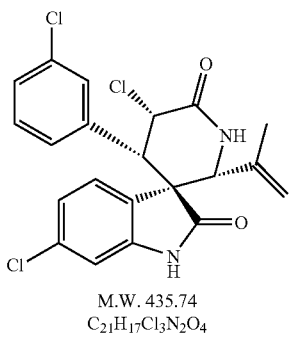

M.W. 435.74
$C_{21}H_{17}Cl_3N_2O_4$

In a manner similar to the method described in Example 4, E/Z-6-chloro-3-(3-chloro-benzylidene)-2-oxo-2,3-dihydro-indole-1-carboxylic acid tert-butyl ester prepared in Example 2 (0.51 g, 1.31 mmol) was reacted with 4-chloro-1-isoprope-nyl-3-trimethylsilyoxy-2-aza-1,3-butadiene (10.5 mmol) in toluene, then treated with trifluoroacetic acid in dichloromethane to give racemic(2'R,3R,4'S, 5'S)-5',6-dichloro-4'-(3-chloro-phenyl)-2'-isopropenyl spiro[3H-indole-3,3'-piperidine]-2,6'(1H)-dione as a yellow solid (Yield 0.3 g, 52%)

EXAMPLE 24

Preparation of racemic(2'R,3R)-6-chloro-4'-(3-chloro-phenyl)-2'-isopropenyl-1',3'-dihydrospiro[3H-indole-3,3'-pyridine]-2,6'(1H)-dione

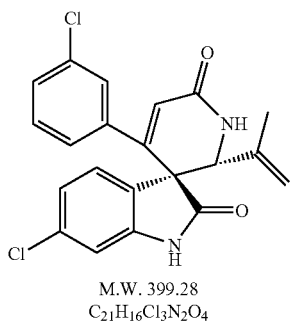

M.W. 399.28
$C_{21}H_{16}Cl_3N_2O_4$

In a manner similar to the method described in Example 5, racemic(2'R,3R,4'S, 5'S)-5',6-dichloro-4'-(3-chloro-phenyl)-2'-isopropenyl spiro[3H-indole-3,3'-piperidine]-2,6'(1H)-dione in Example 24 (0.52 g, 0.69 mmol) was heated with DBU in toluene to give racemic(2'R,3R)-6-chloro-4'-(3-chloro-phenyl)-2'-isopropenyl-1',3'-dihydrospiro[3H-indole-3,3'-pyridine]-2,6'(1H)-dione as a yellow solid (Yield 50 mg, 18%)

HRMS (ES$^+$) m/z Calcd $C_{21}H_{16}Cl_2N_2O_2$+H [(M+H)$^+$]: 399.0662. Found: 399.0663.

EXAMPLE 25

Preparation of intermediate E/Z-6-chloro-3-(3-chloro-benzylidene)-5-fluoro-1,3-dihydro-indol-2-one

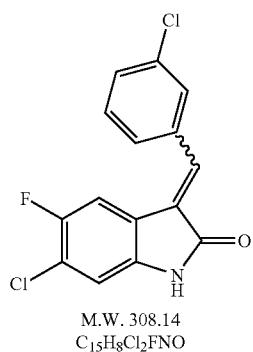

M.W. 308.14
$C_{15}H_8Cl_2FNO$

In a manner similar to the method described in Example 1, 6-chloro-5-fluoro-1,3-dihydro-indol-2-one (0.25 g, 1.35 mmol) (CGENETECH) was reacted with 3-chloro-benzalde-hyde (0.34 g, 2.44 mmol) and pyrrolidine (0.19 g, 2.68 mmol)

in methanol to give a mixture of E- and Z-6-chloro-3-(3-chloro-benzylidene)-5-fluoro-1,3-dihydro-indol-2-one as a yellow solid.

EXAMPLE 26

Preparation of intermediate E/Z-6-chloro-3-(3-chloro-benzylidene)-5-fluoro-2-oxo-2,3-dihydro-indole-1-carboxylic acid tert-butyl ester

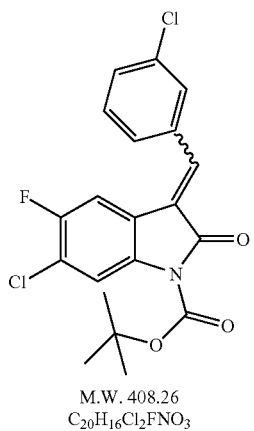

M.W. 408.26
$C_{20}H_{16}Cl_2FNO_3$

In a manner similar to the method described in Example 2, E/Z-6-chloro-3-(3-chloro-benzylidene)-5-fluoro-1,3-dihydro-indol-2-one (0.45 g, 1.46 mmol) was reacted with di-tert-butyl-dicarbonate (0.4 g, 1.83 mmol) (Aldrich), triethyl amine (0.5 g, 4.95 mmol) and 4-dimethylaminopyridine (5 mg) in dichloromethane (30 mL) to give E/Z-6-chloro-3-(3-chloro-benzylidene)-5-fluoro-2-oxo-2,3-dihydro-indole-1-carboxylic acid tert-butyl ester as a yellow solid (Yield: 0.6 g, 100%).

EXAMPLE 27

Preparation of intermediate racemic(2'R,3R,4'S, 5'S)-5',6-dichloro-4'-(3-chloro-phenyl)-5-fluoro-2'-(5-fluoro-2-methyl-phenyl)spiro[3H-indole-3,3'-piperidine]-2,6'(1H)-dione

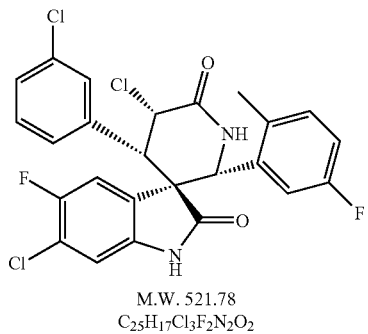

M.W. 521.78
$C_{25}H_{17}Cl_3F_2N_2O_2$

In a manner similar to the method described in Example 4, E/Z-6-chloro-3-(3-chloro-benzylidene)-5-fluoro-2-oxo-2,3-dihydro-indole-1-carboxylic acid tert-butyl ester prepared in Example 26 (0.53 g, 1.31 mmol) was reacted with 4-chloro-1-(5-fluoro-2-methyl-phenyl)-3-trimethylsilyoxy-2-aza-1,3-butadiene prepared in Example 3 (10.5 mmol) in toluene, then treated with trifluoroacetic acid in dichloromethane to give racemic(2'R,3R,4'S, 5'S)-5',6-dichloro-4'-(3-chloro-phenyl)-5-fluoro-2'-(5-fluoro-2-methyl-phenyl)spiro[3H-indole-3,3'-piperidine]-2,6'(1H)-dione as a yellow solid (Yield 0.14 g, 20%)

EXAMPLE 28

Preparation of racemic(2'R,3R)-6-chloro-4'-(3-chloro-phenyl)-5-fluoro-2'-(5-fluoro-2-methyl-phenyl)-1',3'-dihydrospiro[3H-indole-3,3'(2'H)-pyridine]-2,6'(1H)-dione

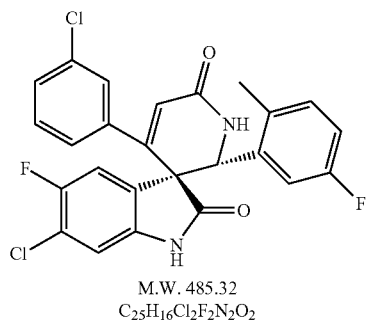

M.W. 485.32
$C_{25}H_{16}Cl_2F_2N_2O_2$

In a manner similar to the method described in Example 5, racemic(2'R,3R,4'S, 5'S)-5',6-dichloro-4'-(3-chloro-phenyl)-5-fluoro-2'-(5-fluoro-2-methyl-phenyl)spiro[3H-indole-3,3'-piperidine]-2,6'(1H)-dione in Example 27 (0.6 g, 1.14 mmol) was heated with DBU in toluene to give racemic(2'R, 3R)-6-chloro-4'-(3-chloro-phenyl)-5-fluoro-2'-(5-fluoro-2-methyl-phenyl)-1',3'-dihydrospiro[3H-indole-3,3'(2'H)-pyridine]-2,6'(1H)-dione as a yellow solid (Yield 40 mg, 7%)

HRMS (ES$^+$) m/z Calcd $C_{25}H_{16}O_2F_2N_2O_2$+H [(M+H)$^+$]: 485.0630. Found: 485.0629.

EXAMPLE 29

Preparation of intermediate E/Z-6-chloro-3-furan-3-ylmethylene-1,3-dihydro-indol-2-one

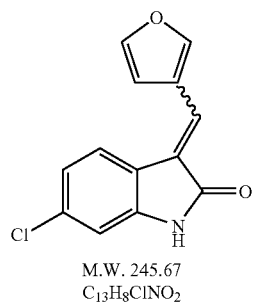

M.W. 245.67
$C_{13}H_8ClNO_2$

In a manner similar to the method described in Example 1, 6-chlorooxindole (2 g, 11.9 mmol) (Alfa) was reacted with 3-furaldehyde (1.04 mL, 11.9 mmol) and piperidine (1.18 mL, 11.9 mmol) in methanol to give E/Z-6-chloro-3-furan-3-ylmethylene-1,3-dihydro-indol-2-one as a yellow solid (Yield 1.45 g, 55%)

EXAMPLE 30

Preparation of intermediate E/Z-6-chloro-3-furan-3-ylmethylene-2-oxo-2,3-dihydro-indole-1-carboxylic acid tert-butyl ester

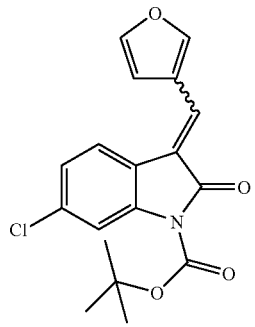

M.W. 345.79
$C_{18}H_{16}ClNO_4$

In a manner similar to the method described in Example 2, E/Z-6-chloro-3-furan-3-ylmethylene-1,3-dihydro-indol-2-one (1.45 g, 5.9 mmol) was reacted with di-tert-butyl-dicarbonate (1.54 g, 7.08 mmol) (Aldrich), and 4-dimethylaminopyridine (25 mg) in dichloromethane to give E/Z-6-chloro-3-furan-3-ylmethylene-2-oxo-2,3-dihydro-indole-1-carboxylic acid tert-butyl ester as a yellow solid (Yield: 1.6 g, 79%).

EXAMPLE 31

Preparation of intermediate racemic(2'R,3R,4'S, 5'S)-5',6-dichloro-2'-(5-fluoro-2-methyl-phenyl)-4'-(furan-3-yl)spiro[3H-indole-3,3'-piperidine]-2,6'(1H)-dione

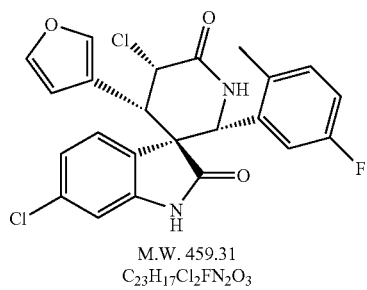

M.W. 459.31
$C_{23}H_{17}Cl_2FN_2O_3$

In a manner similar to the method described in Example 4, E/Z-6-chloro-3-furan-3-ylmethylene-2-oxo-2,3-dihydro-indole-1-carboxylic acid tert-butyl ester prepared in Example 30 (0.91 g, 2.62 mmol) was reacted with 4-chloro-1-(5-fluoro-2-methyl-phenyl)-3-trimethylsilyoxy-2-aza-1,3-butadiene prepared in Example 3 (21 mmol) in toluene, then treated with trifluoroacetic acid in dichloromethane to give racemic(2'R,3R,4'S, 5'S)-5',6-dichloro-2'-(5-fluoro-2-me-thyl-phenyl)-4'-(furan-3-yl)spiro[3H-indole-3,3'-piperidine]-2,6'(1H)-dione as a yellow solid (Yield 0.25 g, 21%)

EXAMPLE 32

Preparation of racemic(2'R,3R)-6-chloro-2'-(5-fluoro-2-methyl-phenyl)-4'-(furan-3-yl)-1',3'-dihydrospiro[3H-indole-3,3'(2'H)-pyridine]-2,6'(1H)-dione

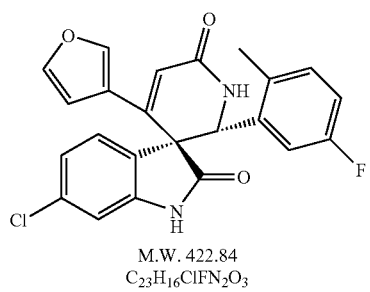

M.W. 422.84
$C_{23}H_{16}ClFN_2O_3$

In a manner similar to the method described in Example 5, racemic(2'R,3R,4'S, 5'S)-5',6-dichloro-2'-(5-fluoro-2-methyl-phenyl)-4'-(furan-3-yl)spiro[3H-indole-3,3'-piperidine]-2,6'(1H)-dione in Example 31 (0.25 g, 0.54 mmol) was heated with DBU in toluene to give racemic(2'R,3R)-6-chloro-2'-(5-fluoro-2-methyl-phenyl)-4'-(furan-3-yl)-1',3'-dihydrospiro[3H-indole-3,3'(2'H)-pyridine]-2,6'(1H)-dione as a yellow solid (Yield 40 mg, 18%)

HRMS (ES$^+$) m/z Calcd $C_{23}H_{16}ClFN_2O_3$+H [(M+H)$^+$]: 423.0906. Found: 423.0906.

EXAMPLE 33

Preparation of intermediate E/Z-6-chloro-3-thiophen-3-ylmethylene-1,3-dihydro-indol-2-one

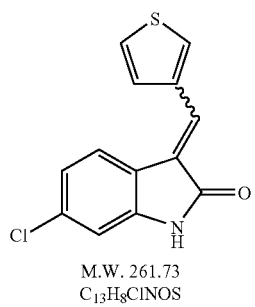

M.W. 261.73
$C_{13}H_8ClNOS$

In a manner similar to the method described in Example 1, 6-chlorooxindole (2 g, 11.9 mmol) (Alfa) was reacted with 3-thiophenecarboxaldehyde (1.09 mL, 11.9 mmol) (Aldrich) and piperidine (1.18 mL, 11.9 mmol) in methanol to give E/Z-6-chloro-3-thiophen-3-ylmethylene-1,3-dihydro-indol-2-one as a yellow solid (Yield 2.4 g, 77%)

EXAMPLE 34

Preparation of intermediate E/Z-6-chloro-2-oxo-3-thiophen-3-ylmethylene-2,3-dihydro-indole-1-carboxylic acid tert-butyl ester

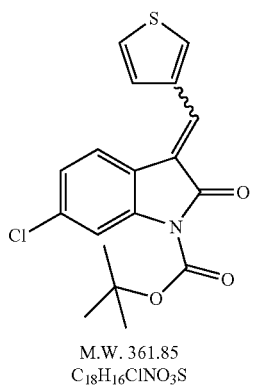

M.W. 361.85
C$_{18}$H$_{16}$ClNO$_3$S

In a manner similar to the method described in Example 2, E/Z-6-chloro-3-thiophen-3-ylmethylene-1,3-dihydro-indol-2-one (2.4 g, 9.17 mmol) was reacted with di-tert-butyl-dicarbonate (2.4 g, 11 mmol) (Aldrich), and 4-dimethylaminopyridine (45 mg) in dichloromethane to give E/Z-6-chloro-2-oxo-3-thiophen-3-ylmethylene-2,3-dihydro-indole-1-carboxylic acid tert-butyl ester as a yellow solid (Yield: 2 g, 60%).

EXAMPLE 35

Preparation of intermediate racemic(2'R,3R,4'S, 5'S)-5',6-dichloro-2'-(5-fluoro-2-methyl-phenyl)-4'-(thiophen-3-yl)spiro[3H-indole-3,3'-piperidine]-2,6'(1H)-dione

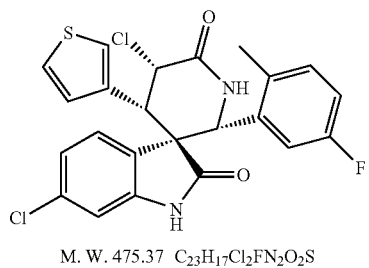

M. W. 475.37  C$_{23}$H$_{17}$Cl$_2$FN$_2$O$_2$S

In a manner similar to the method described in Example 4, E/Z-6-chloro-2-oxo-3-thiophen-3-ylmethylene-2,3-dihydro-indole-1-carboxylic acid tert-butyl ester prepared in Example 34 (0.95 g, 2.6 mmol) was reacted with 4-chloro-1-(5-fluoro-2-methyl-phenyl)-3-trimethylsilyoxy-2-aza-1,3-butadiene prepared in Example 3 (21 mmol) in toluene, then treated with trifluoroacetic acid in dichloromethane to give racemic(2'R,3R,4'S, 5'S)-5',6-dichloro-2'-(5-fluoro-2-methyl-phenyl)-4'-(thiophen-3-yl)spiro[3H-indole-3,3'-piperidine]-2,6'(1H)-dione as a yellow solid (Yield 0.3 g, 24%)

EXAMPLE 36

Preparation of racemic(2'R,3R)-6-chloro-2'-(5-fluoro-2-methyl-phenyl)-4'-(thiophen-3-yl)-1',3'-dihydrospiro[3H-indole-3,3'(2'H)-pyridine]-2,6'(1H)-dione

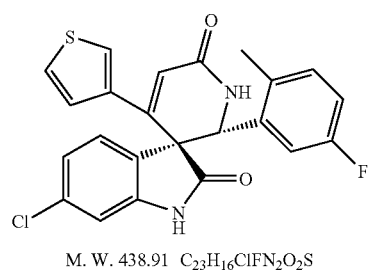

M. W. 438.91  C$_{23}$H$_{16}$ClFN$_2$O$_2$S

In a manner similar to the method described in Example 5, racemic(2'R,3R,4'S, 5'S)-5',6-dichloro-2'-(5-fluoro-2-methyl-phenyl)-4'-(thiophen-3-yl)spiro[3H-indole-3,3'-piperidine]-2,6'(1H)-dione in Example 35 (0.3 g, 0.63 mmol) was heated with DBU in toluene to give racemic(2'R,3R)-6-chloro-2'-(5-fluoro-2-methyl-phenyl)-4'-(thiophen-3-yl)-1',3'-dihydrospiro[3H-indole-3,3'(2'H)-pyridine]-2,6'(1H)-dione as a yellow solid (Yield 80 mg, 29%)

HRMS (ES$^+$) m/z Calcd C$_{23}$H$_{16}$ClFN$_2$O$_2$S+H [(M+H)$^+$]: 439.0678. Found: 439.0676.

EXAMPLE 37

Preparation of intermediate E/Z-6-chloro-3-pyridin-3-ylmethylene-1,3-dihydro-indol-2-one

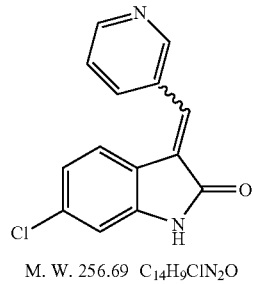

M. W. 256.69  C$_{14}$H$_9$ClN$_2$O

In a manner similar to the method described in Example 1, 6-chlorooxindole (2 g, 11.9 mmol) (Alfa) was reacted with nicotinaldehyde (1.13 mL, 11.9 mmol) (Aldrich) and piperidine (1.18 mL, 11.9 mmol) in methanol to give E/Z-6-chloro-3-pyridin-3-ylmethylene-1,3-dihydro-indol-2-one as a yellow solid (Yield 2.3 g, 75%)

EXAMPLE 38

Preparation of intermediate E/Z-6-chloro-2-oxo-3-pyridin-3-ylmethylene-2,3-dihydro-indole-1-carboxylic acid tert-butyl ester

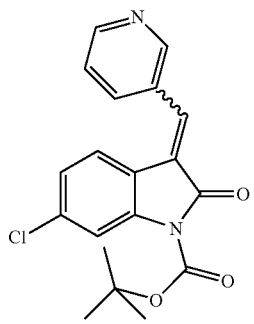

M. W. 356.81  $C_{19}H_{17}ClN_2O_3$

In a manner similar to the method described in Example 2, E/Z-6-chloro-3-pyridin-3-ylmethylene-1,3-dihydro-indol-2-one (2.3 g, 8.96 mmol) was reacted with di-tert-butyl-dicarbonate (2.34 g, 10.7 mmol) (Aldrich), and 4-dimethylaminopyridine (44 mg) in dichloromethane to give E/Z-6-chloro-2-oxo-3-pyridin-3-ylmethylene-2,3-dihydro-indole-1-carboxylic acid tert-butyl ester as a yellow solid (Yield: 2 g, 60%).

EXAMPLE 39

Preparation of intermediate racemic(2'R,3R,4'S,5'S)-5',6-dichloro-2'-(5-fluoro-2-methyl-phenyl)-4'-(pyridin-3-yl)spiro[3H-indole-3,3'-piperidine]-2,6'(1H)-dione

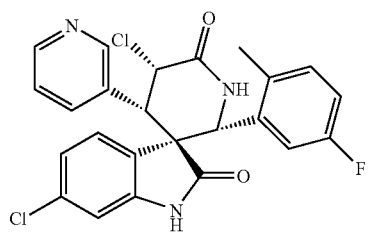

M. W. 470.33  $C_{24}H_{18}Cl_2FN_3O_2$

In a manner similar to the method described in Example 4, E/Z-6-chloro-2-oxo-3-pyridin-3-ylmethylene-2,3-dihydro-indole-1-carboxylic acid tert-butyl ester prepared in Example 38 (0.94 g, 2.63 mmol) was reacted with 4-chloro-1-(5-fluoro-2-methyl-phenyl)-3-trimethylsilyoxy-2-aza-1,3-butadiene prepared in Example 3 (21 mmol) in toluene, then treated with trifluoroacetic acid in dichloromethane to give racemic(2'R,3R,4'S, 5'S)-5',6-dichloro-2'-(5-fluoro-2-methyl-phenyl)-4'-(pyridin-3-yl)spiro[3H-indole-3,3'-piperidine]-2,6'(1H)-dione as a yellow solid (Yield 0.45 g, 36%)

EXAMPLE 40

Preparation of racemic(2'R,3R)-6-chloro-2'-(5-fluoro-2-methyl-phenyl)-4'-(pyridin-3-yl)-1',3'-dihydrospiro[3H-indole-3,3'(2'H)-pyridine]-2,6'(1H)-dione

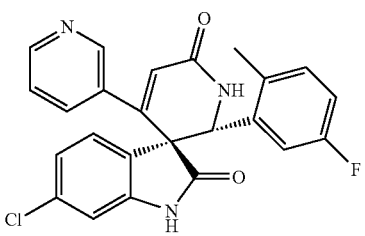

M. W. 433.87  $C_{24}H_{17}ClFN_3O_2$

In a manner similar to the method described in Example 5, racemic(2'R,3R,4'S, 5'S)-5',6-dichloro-2'-(5-fluoro-2-methyl-phenyl)-4'-(pyridin-3-yl)spiro[3H-indole-3,3'-piperidine]-2,6'(1H)-dione in Example 39 (0.45 g, 0.96 mmol) was heated with DBU in toluene to give racemic(2'R,3R)-6-chloro-2'-(5-fluoro-2-methyl-phenyl)-4'-(pyridin-3-yl)-1',3'-dihydrospiro[3H-indole-3,3'(2'H)-pyridine]-2,6'(1H)-dione as a white solid (Yield 70 mg, 17%)

HRMS (ES$^+$) m/z Calcd $C_{24}H_{17}ClFN_3O_2$+H [(M+H)$^+$]: 434.1066. Found: 434.1065.

EXAMPLE 41

Preparation of intermediate 5-iodo-2-(tetrahydro-pyran-4-yloxy)-benzaldehyde

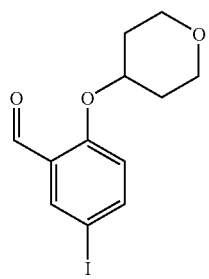

M. W. 332.14  $C_{12}H_{13}IO_3$

In a manner similar to the method described in Example 9, 5-iodosalicylaldehyde (3 g, 12.1 mmol) (Aldrich) reacted with methanesulfonic acid tetrahydropyran-4-yl ester (4 g, 22 mmol) and $K_2CO_3$ in N,N-dimethylformamide to give 5-iodo-2-(tetrahydro-pyran-4-yloxy)-benzaldehyde as a yellow solid (Yield 3.4 g, 85%).

EXAMPLE 42

Preparation of intermediate 4-chloro-1-[5-iodo-2-(tetrahydro-pyran-4-yloxy)-phenyl]-3-trimethylsilyoxy-2-aza-1,3-butadiene

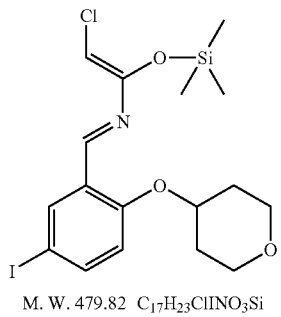

M. W. 479.82 C$_{17}$H$_{23}$ClINO$_3$Si

In a manner similar to the method described in Example 3, 5-iodo-2-(tetrahydro-pyran-4-yloxy)-benzaldehyde (6.97 g, 21 mmol) was reacted with 1,1,1,3,3,3-hexamethyldisilazane (4.38 mL, 21 mmol), n-butyllithium (2.5 M, 8.4 mL, 21 mmol), trimethylsilyl chloride (2.66 mL, 21 mmol), triethylamine (3.78 mL, 27 mmol) and chloroacetyl chloride (2.18 mL, 27 mmol) to give crude 4-chloro-1-[5-iodo-4-2-(tetrahydro-pyran-4-yloxy)-phenyl]-3-trimethylsilyoxy-2-aza-1,3-butadiene as a yellow gum and used for the next step without further purification.

EXAMPLE 43

Preparation of intermediate racemic(2'R,3R,4'S, 5'S)-5',6-dichloro-4'-(3-chloro-phenyl)-2'-[5-iodo-2-(tetrahydro-pyran-4-yloxy)-phenyl]spiro[3H-indole-3,3'-piperidine]-2,6'(1H)-dione

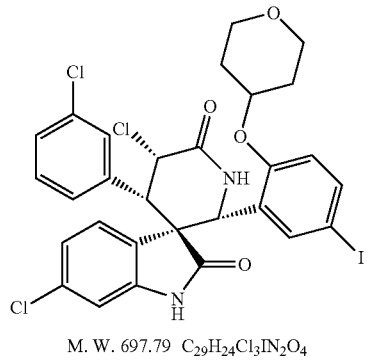

M. W. 697.79 C$_{29}$H$_{24}$Cl$_3$IN$_2$O$_4$

In a manner similar to the method described in Example 4, E/Z-6-chloro-3-(3-chloro-benzylidene)-2-oxo-2,3-dihydro-indole-1-carboxylic acid tert-butyl ester prepared in Example 2 (1.02 g, 2.63 mmol) was reacted with 4-chloro-1-[5-iodo-2-(tetrahydro-pyran-4-yloxy)-phenyl]-3-trimethylsilyoxy-2-aza-1,3-butadiene (21 mmol) in toluene, then treated with trifluoroacetic acid in dichloromethane to give racemic(2'R, 3R,4'S, 5'S)-5',6-dichloro-4'-(3-chloro-phenyl)-2'-[5-iodo-2-(tetrahydro-pyran-4-yloxy)-phenyl]spiro[3H-indole-3,3'-piperidine]-2,6'(1H)-dione as a yellow solid (Yield 0.3 g, 16%)

EXAMPLE 44

Preparation of racemic(2'R,3R)-6-chloro-4'-(3-chloro-phenyl)-2'-[5-iodo-2-(tetrahydro-pyran-4-yloxy)-phenyl]-1',3'-dihydrospiro[3H-indole-3,3'-pyridine]-2,6'(1H)-dione

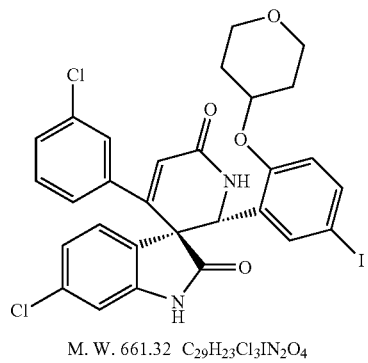

M. W. 661.32 C$_{29}$H$_{23}$Cl$_3$IN$_2$O$_4$

In a manner similar to the method described in Example 5, racemic(2'R,3R,4'S, 5'S)-5',6-dichloro-2'-[5-chloro-2-(tetrahydro-pyran-4-yloxy)-phenyl]-4'-(3-chlorophenyl) spiro [3H-indole-3,3'-piperidine]-2,6'(1H)-dione in Example 43 (0.3 g, 0.43 mmol) was heated with DBU in toluene to give racemic(2'R,3R,4'S, 5'S)-5',6-dichloro-4'-(3-chloro-phenyl)-2'-[5-iodo-2-(tetrahydro-pyran-4-yloxy)-phenyl]spiro[3H-indole-3,3'-piperidine]-2,6'(1H)-dione as a yellow solid (Yield 140 mg, 43%)

HRMS (ES$^+$) m/z Calcd C$_{29}$H$_{23}$Cl$_3$IN$_2$O$_4$+H [(M+H)$^+$]: 661.0153. Found: 661.0156.

EXAMPLE 45

Preparation of racemic(2'R,3R)-6-chloro-4'-(3-chloro-phenyl)-2'-[5-ethynyl-2-(tetrahydro-pyran-4-yloxy)-phenyl]-1',3'-dihydrospiro[3H-indole-3,3'-pyridine]-2,6'(1H)-dione

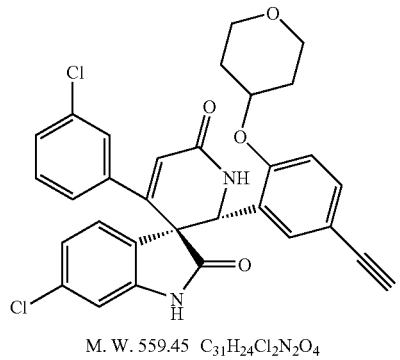

M. W. 559.45 C$_{31}$H$_{24}$Cl$_2$N$_2$O$_4$

A solution of racemic(2'R,3R,4'S, 5'S)-5',6-dichloro-4'-(3-chloro-phenyl)-2'-[5-iodo-2-(tetrahydro-pyran-4-yloxy)-phenyl]spiro[3H-indole-3,3'-piperidine]-2,6'(1H)-dione (0.1 g, 0.15 mmol) prepared in Example 44 in anhydrous N,N-dimethylformamide (3 mL) was added trimethylsilyl acetylene (0.15 g, 1.5 mmol) (Aldrich), CuI (3 mg) (Aldrich) and triethylamine (0.63 mL, 4.5 mmol). The mixture was degassed under nitrogen for 5 min, then dichlorobis(triphenylphosphine) palladium(0) (8.4 mg, 0.012 mmol) (Strem) was added and the reaction mixture was heated at 80° C. under nitrogen for 40 min. The reaction mixture was partitioned between ethyl acetate and water. The organic layer was separated, washed with water twice, dried over MgSO$_4$, and concentrated. To the residue was added methanol (2 mL) and aqueous NaOH solution (2 N, 2 mL). The mixture was stirred at room temperature for 1 h, then partitioned between ethyl acetate and water. The organic layer was separated, and the aqueous layer was extracted with ethyl acetate. The organic layers were combined, washed with water, brine, dried over MgSO$_4$ and concentrated to give racemic(2'R,3R)-6-chloro-4'-(3-chloro-phenyl)-2'-[5-ethynyl-2-(tetrahydro-pyran-4-yloxy)-phenyl]-1',3'-dihydrospiro[3H-indole-3,3'-pyridine]-2,6'(1H)-dione as a yellow solid (Yield 24 mg, 30%). HRMS (ES$^+$) m/z Calcd for C$_{31}$H$_{24}$Cl$_2$N$_2$O$_4$+H [(M+H)$^+$]: 559.1186. Found: 559.1186.

EXAMPLE 46

Preparation of intermediate racemic(2'S,3R,4'S, 5'S)-5',6-dichloro-4'-(3-chloro-phenyl)-2'-[5-iodo-2-(tetrahydro-pyran-4-yloxy)-phenyl]spiro[3H-indole-3,3'-piperidine]-2,6'(1H)-dione

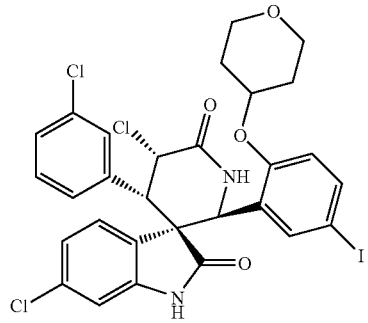

M. W. 697.79 C$_{29}$H$_{24}$Cl$_3$IN$_2$O$_4$

In the preparation of racemic(2'R,3R,4'S, 5'S)-5',6-dichloro-4'-(3-chloro-phenyl)-2'-[5-iodo-2-(tetrahydro-pyran-4-yloxy)-phenyl]spiro[3H-indole-3,3'-piperidine]-2,6'(1H)-dione in Example 43, racemic(2'S,3R,4'S, 5'S)-5',6-dichloro-4'-(3-chloro-phenyl)-2'-[5-iodo-2-(tetrahydro-pyran-4-yloxy)-phenyl]spiro[3H-indole-3,3'-piperidine]-2,6'(1H)-dione was obtained as the second product: a yellow solid (Yield 0.15 g, 8%)

EXAMPLE 47

Preparation of intermediate racemic(2'S,3R)-6-chloro-4'-(3-chloro-phenyl)-2'-[5-iodo-2-(tetrahydro-pyran-4-yloxy)-phenyl]-1',3'-dihydrospiro[3H-indole-3,3'-pyridine]-2,6'(1H)-dione

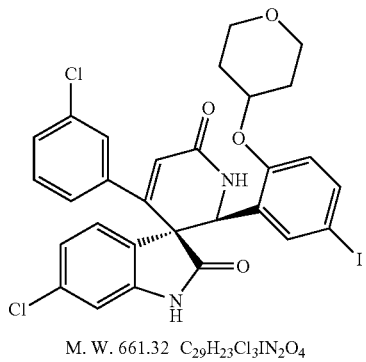

M. W. 661.32 C$_{29}$H$_{23}$Cl$_3$IN$_2$O$_4$

In a manner similar to the method described in Example 44, racemic(2'S,3R,4'S, 5'S)-5',6-dichloro-2'-[5-chloro-2-(tetrahydro-pyran-4-yloxy)-phenyl]-4'-(3-chlorophenyl) spiro[3H-indole-3,3'-piperidine]-2,6'(1H)-dione in Example 46 (0.15 g, 0.22 mmol) was heated with DBU in toluene to give racemic(2'R,3R,4'S, 5'S)-5',6-dichloro-4'-(3-chloro-phenyl)-2'-[5-iodo-2-(tetrahydro-pyran-4-yloxy)-phenyl]spiro[3H-indole-3,3'-piperidine]-2,6'(1H)-dione as a yellow solid (Yield 29 mg, 20%)

EXAMPLE 48

Preparation of racemic(2'S,3R)-6-chloro-4'-(3-chloro-phenyl)-2'-[5-ethynyl-2-(tetrahydro-pyran-4-yloxy)-phenyl]-1',3'-dihydrospiro[3H-indole-3,3'-pyridine]-2,6'(1H)-dione

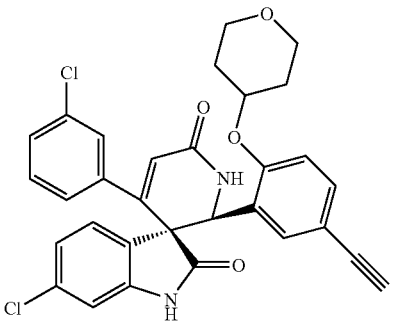

M. W. 559.45 C$_{31}$H$_{24}$Cl$_2$N$_2$O$_4$

In a manner similar to the method described in Example 45, racemic(2'S,3R,4'S)-6-chloro-4'-(3-chlorophenyl)-2'-[5-Iodo-2-(tetrahydro-pyran-4-yloxy)-phenyl]spiro[3H-indole-3,3'-piperidine]-2,6'(1H)-dione (29 mg, 0.043 mmol) was reacted with trimethylsilyl acetylene (43 mg, 0.43 mmol), CuI (8 mg, 0.043 mmol), triethylamine (44 uL, 0.043 mmol) and dichlorobis(triphenylphosphine) palladium(0) (6 mg, 0.08 mmol), then treated with aqueous NaOH solution in methanol to give racemic(2'S,3R)-6-chloro-4'-(3-chloro-phenyl)-2'-[5-ethynyl-2-(tetrahydro-pyran-4-yloxy)-phenyl]-1',3'-dihydrospiro[3H-indole-3,3'-pyridine]-2,6'(1H)-dione as an off white solid (Yield 12 mg, 50%).
HRMS (ES$^+$) m/z Calcd for C$_{31}$H$_{24}$Cl$_2$N$_2$O$_4$+H [(M+H)$^+$]: 559.1186. Found: 559.1183.

EXAMPLE 49

Preparation of intermediate E/Z-6-chloro-3-(5-chloro-furan-2-ylmethylene)-1,3-dihydro-indol-2-one

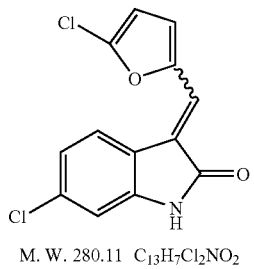

M.W. 280.11  $C_{13}H_7Cl_2NO_2$

In a manner similar to the method described in Example 1, 6-chlorooxindole (3.2 g, 19.1 mmol) (Alfa) was reacted with 5-chloro-2-furaldehyde (2.5 g, 19.1 mmol) (Aldrich) and piperidine (1.89 mL, 19.1 mmol) in methanol to give E/Z-6-chloro-3-(5-chloro-furan-2-ylmethylene)-1,3-dihydro-indol-2-one as a yellow solid (Yield 5.2 g, 97%)

EXAMPLE 50

Preparation of intermediate E/Z-6-chloro-3-(5-chloro-furan-2-ylmethylene)-2-oxo-2,3-dihydro-indole-1-carboxylic acid tert-butyl ester

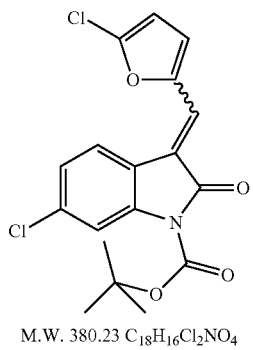

M.W. 380.23  $C_{18}H_{16}Cl_2NO_4$

In a manner similar to the method described in Example 2, E/Z-6-chloro-3-(5-chloro-furan-2-ylmethylene)-1,3-dihydro-indol-2-one (5.2 g, 22.3 mmol) was reacted with di-tert-butyl-dicarbonate (4.86 g, 22.2 mmol) (Aldrich), and 4-dimethylaminopyridine (91 mg) in dichloromethane to give E/Z-6-chloro-3-(5-chloro-furan-2-ylmethylene)-2-oxo-2,3-dihydro-indole-1-carboxylic acid tert-butyl ester as a yellow solid (Yield: 6.1 g, 87%).

EXAMPLE 51

Preparation of intermediate racemic(2'R,3R,4'S, 5'S)-5',6-dichloro-4'-(5-chloro-furan-2-ylmethylene)-2'-(5-fluoro-2-methyl-phenyl)spiro[3H-indole-3,3'-piperidine]-2,6'(1H)-dione

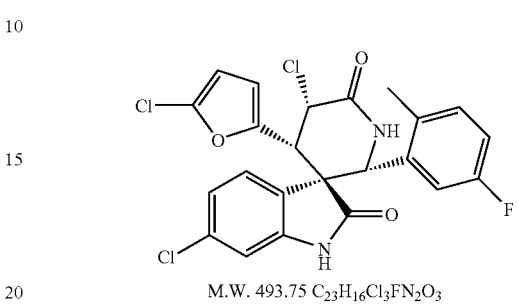

M.W. 493.75  $C_{23}H_{16}Cl_3FN_2O_3$

In a manner similar to the method described in Example 4, E/Z-6-chloro-3-(5-chloro-furan-2-ylmethylene)-2-oxo-2,3-dihydro-indole-1-carboxylic acid tert-butyl ester prepared in Example 50 (1.33 g, 3.5 mmol) was reacted with 4-chloro-1-(5-fluoro-2-methyl-phenyl)-3-trimethylsilyoxy-2-aza-1,3-butadiene prepared in Example 3 (21 mmol) in toluene, then treated with trifluoroacetic acid in dichloromethane to give racemic(2'R,3R,4'S, 5'S)-5',6-dichloro-4'-(5-chloro-furan-2-ylmethylene)-2'-(5-fluoro-2-methyl-phenyl)spiro[3H-indole-3,3'-piperidine]-2,6'(1H)-dione as a yellow solid (Yield 0.3 g, 17%)

EXAMPLE 52

Preparation of racemic(2'R,3R)-6-chloro-4'-(5-chloro-furan-2-ylmethylene)-2'-(5-fluoro-2-methyl-phenyl)-1',3'-dihydrospiro[3H-indole-3,3'(2'H)-pyridine]-2,6'(1H)-dione

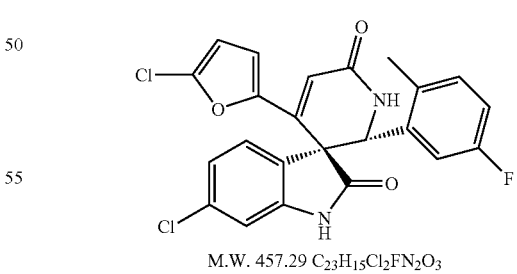

M.W. 457.29  $C_{23}H_{15}Cl_2FN_2O_3$

In a manner similar to the method described in Example 5, racemic(2'R,3R,4'S, 5'S)-5',6-dichloro-4'-(5-chloro-furan-2-ylmethylene)-2'-(5-fluoro-2-methyl-phenyl) spiro[3H-indole-3,3'-piperidine]-2,6'(1H)-dione in Example 51 (0.3 g, 0.6 mmol) was heated with DBU in toluene to give racemic (2'R,3R)-6-chloro-4'-(5-chloro-furan-2-ylmethylene)-2'-(5-fluoro-2-methyl-phenyl)-1',3'-dihydrospiro[3H-indole-3,3'(2'H)-pyridine]-2,6'(1H)-dione as a yellow solid (Yield 65 mg, 24%)

HRMS (ES+) m/z Calcd $C_{23}H_{15}Cl_2FN_2O_3$+H [(M+H)+]: 320.1493. Found: 320.1493.

EXAMPLE 53

Preparation of intermediate cyclopent-1-enecarbaldehyde

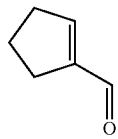

M.W. 96.13 $C_6H_8O$

To an acidic solution of sodium periodate (28.3 g, 0.13 mol) (Aldrich) in water (250 mL) was added the solution of 1,2-cyclohexanediol (12 g, 0.10 mol) (Acros) in ethyl ether (150 mL). The mixture was stirred vigorously for 0.5 h at room temperature. After addition of KOH aqueous solution (20%, 38.4 mL), the reaction mixture was stirred for an additional 1 h. The mixture was extracted with ethyl ether. The organic layers were combined and dried. The solvent was removed to give cyclopent-1-enecarbaldehyde as yellow oil (Yield: 7.2 g, 75%)

EXAMPLE 54

Preparation of intermediate E/Z-6-chloro-3-cyclopent-1-enylmethylene-1,3-dihydro-indol-2-one

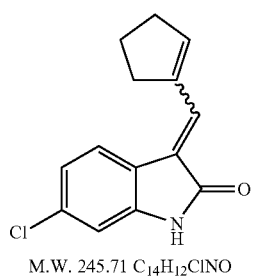

M.W. 245.71 $C_{14}H_{12}ClNO$

In a manner similar to the method described in Example 1, 6-chlorooxindole (2.51 g, 15 mmol) (Alfa) was reacted with cyclopent-1-enecarbaldehyde (1.45 g, 15 mmol) (Aldrich) and piperidine (1.49 mL, 15 mmol) in methanol to give E/Z-6-chloro-3-cyclopent-1-enylmethylene-1,3-dihydro-indol-2-one as a yellow solid (Yield 1.13 g, 30%)

EXAMPLE 55

Preparation of intermediate E/Z-6-Chloro-3-cyclopent-1-enylmethylene-2-oxo-2,3-dihydro-indole-1-carboxylic acid tert-butyl ester

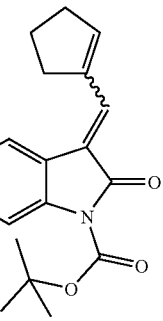

M.W. 345.83 $C_{19}H_{20}ClNO_3$

In a manner similar to the method described in Example 2, E/Z-6-chloro-3-cyclopent-1-enylmethylene-1,3-dihydro-indol-2-one (1.13 g, 4.6 mmol) was reacted with di-tert-butyl-dicarbonate (1.1 g, 5.1 mmol) (Aldrich), and 4-dimethylaminopyridine (23 mg) in dichloromethane to give E/Z-6-Chloro-3-cyclopent-1-enylmethylene-2-oxo-2,3-dihydro-indole-1-carboxylic acid tert-butyl ester ester as a yellow solid (Yield: 1.5 g, 94%).

EXAMPLE 56

Preparation of intermediate racemic(2'R,3R,4'S,5'S)-5',6-dichloro-4'-(cyclopent-1-enyl)-2'-(5-fluoro-2-methyl-phenyl)spiro[3H-indole-3,3'-piperidine]-2,6'(1H)-dione

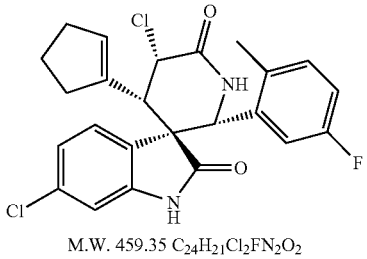

M.W. 459.35 $C_{24}H_{21}Cl_2FN_2O_2$

In a manner similar to the method described in Example 4, E/Z-6-Chloro-3-cyclopent-1-enylmethylene-2-oxo-2,3-dihydro-indole-1-carboxylic acid tert-butyl ester ester prepared in Example 55 (1.21 g, 3.5 mmol) was reacted with 4-chloro-1-(5-fluoro-2-methyl-phenyl)-3-trimethylsilyoxy-2-aza-1,3-butadiene prepared in Example 3 (21 mmol) in toluene, then treated with trifluoroacetic acid in dichloromethane to give racemic(2'R,3R,4'S, 5'S)-5',6-dichloro-4'-(cyclopent-1-enyl)-2'-(5-fluoro-2-methyl-phenyl)spiro[3H-indole-3,3'-piperidine]-2,6'(1H)-dione as a yellow solid (Yield 0.3 g, 19%)

EXAMPLE 57

Preparation of racemic(2'R,3R)-6-chloro-4'-(cyclopent-1-enyl)-2'-(5-fluoro-2-methyl-phenyl)-1',3'-dihydrospiro[3H-indole-3,3'(2'H)-pyridine]-2,6'(1H)-dione

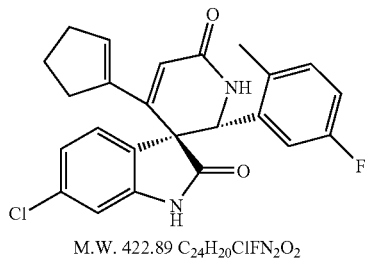

M.W. 422.89 C$_{24}$H$_{20}$ClFN$_2$O$_2$

In a manner similar to the method described in Example 5, racemic(2'R,3R,4'S, 5'S)-5',6-dichloro-4'-(cyclopent-1-enyl)-2'-(5-fluoro-2-methyl-phenyl)spiro[3H-indole-3,3'-piperidine]-2,6'(1H)-dione in Example 56 (0.3 g, 0.65 mmol) was heated with DBU in toluene to give racemic(2'R,3R)-6-chloro-4'-(cyclopent-1-enyl)-2'-(5-fluoro-2-methyl-phenyl)-1',3'-dihydrospiro[3H-indole-3,3'(2'H)-pyridine]-2,6'(1H)-dione as a yellow solid (Yield 25 mg, 9%)

HRMS (ES$^+$) m/z Calcd C$_{24}$H$_{20}$ClFN$_2$O$_2$+H [(M+H)$^+$]: 551.1279. Found: 551.1278.

EXAMPLE 58

Preparation of intermediate 2-(4-chloro-2-formyl-phenoxy)-2-methyl-propionic acid tert-butyl ester

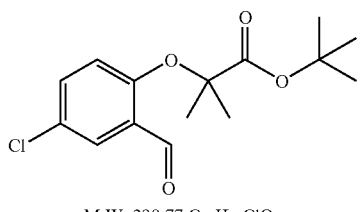

M.W. 298.77 C$_{15}$H$_{19}$ClO$_4$

To a solution of 5-chlorosalicylaldehyde (5 g, 32 mmol) in N,N-dimethylformamide (100 mL) was added 2-bromo-2-methyl-propionic acid tert-butyl ester (10.7 g, 48 mmol), Cs$_2$CO$_3$ (3.1 g, 95 mmol). The reaction mixture was heated at 140° C. for 18 h. The mixture was partitioned between ethyl acetate and water. The organic layer was separated, and aqueous layer was extracted with ethyl acetate. The organic layers were combined, washed with water, brine, dried over Na$_2$SO$_4$ and concentrated to give 2-(4-chloro-2-formyl-phenoxy)-2-methyl-propionic acid tert-butyl ester as a pale yellow solid (Yield 5.2 g, 54%)

EXAMPLE 59

Preparation of intermediate E/Z-2-[4-chloro-2-(6-chloro-2-oxo-1,2-dihydro-indol-3-ylidenemethyl)-phenoxy]-2-methyl-propionic acid tert-butyl ester

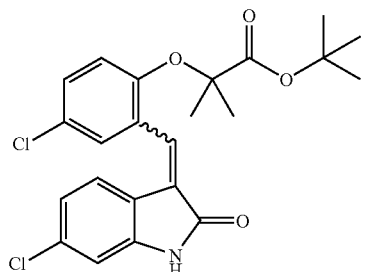

M.W. 448.55 C$_{23}$H$_{23}$Cl$_2$NO$_4$

To a mixture of 2-(4-chloro-2-formyl-phenoxy)-2-methyl-propionic acid tert-butyl ester (5.17 g, 17.3 mmol) and 6-chlorooxindole (2.89 g, 17.3 mmol) were anhydrous methanol (100 mL) at room temperature was slowly added piperidine (1.7 mL, 17.3 mmol). The reaction mixture was heated at 70° C. for 0.5 h. Then the mixture was cooled to room temperature and filtered. The precipitate was dried and collected to give E/Z-2-[4-chloro-2-(6-chloro-2-oxo-1,2-dihydro-indol-3-ylidenemethyl)-phenoxy]-2-methyl-propionic acid tert-butyl ester as a yellow solid (Yield 6.5 g, 84%).

EXAMPLE 60

Preparation of intermediate E/Z-3-[2-(1-tert-butoxycarbonyl-1-methyl-ethoxy)-5-chloro-benzylidene]-6-chloro-2-oxo-2,3-dihydro-indole-1-carboxylic acid tert-butyl ester

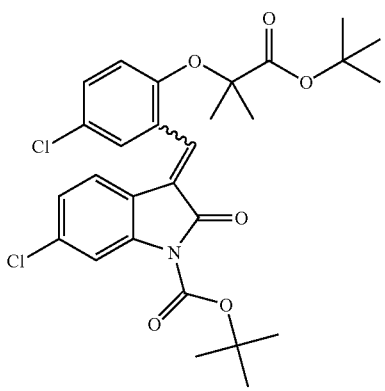

M.W. 533.43 C$_{27}$H$_{28}$Cl$_2$NO$_6$

In a manner similar to the method described in Example 2, E/Z-2-[4-chloro-2-(6-chloro-2-oxo-1,2-dihydro-indol-3-ylidenemethyl)-phenoxy]-2-methyl-propionic acid tert-butyl ester (6.5 g, 14.5 mmol) was reacted with di-tert-butyl-dicarbonate (3.79 g, 17.4 mmol) (Aldrich), and 4-dimethylaminopyridine (71 mg) in dichloromethane to give E/Z-3-[2-(1-tert-butoxycarbonyl-1-methyl-ethoxy)-5-chloro-benzylidene]-6-chloro-2-oxo-2,3-dihydro-indole-1-carboxylic acid tert-butyl ester as a yellow solid (Yield: 6.9 g, 87%).

EXAMPLE 61

Preparation of intermediate racemic(2'S,3S,4'R,5'R)-4'-[2-(1-tert-butoxycarbonyl-1-methyl-ethoxy)-5-chloro-phenyl]-5',6-dichloro-2'-(5-fluoro-2-methyl-phenyl)spiro[3H-indole-3,3'-piperidine]-2,6'(1H)-dione

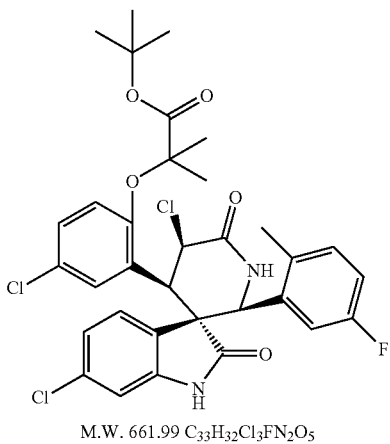

M.W. 661.99 C$_{33}$H$_{32}$Cl$_3$FN$_2$O$_5$

To a solution of 4-chloro-1-(5-fluoro-2-methyl-phenyl)-3-trimethylsilyoxy-2-aza-1,3-butadiene prepared in Example 3 (21 mmol) in toluene (30 mL) was added E/Z-3-[2-(1-tert-butoxycarbonyl-1-methyl-ethoxy)-5-chloro-benzylidene]-6-chloro-2-oxo-2,3-dihydro-indole-1-carboxylic acid tert-butyl ester prepared in Example 60 (1.92 g, 3.5 mmol). The reaction mixture was stirred in a sealed tube under nitrogen at 140° C. for 1 h, then 120° C. for 4 h. After the solution was cooled to room temperature, methanol (10 mL) was added. The reaction mixture was concentrated. The residue was purified by chromatography (EtOAc:CH$_2$Cl$_2$=1; 19, 1:9) to give racemic(2'S,3S,4'R,5'R)-4'-[2-(1-tert-butoxycarbonyl-1-methyl-ethoxy)-5-chloro-phenyl]-5',6-dichloro-2'-(5-fluoro-2-methyl-phenyl)spiro[3H-indole-3,3'-piperidine]-2,6'(1H)-dione as an off-white solid (Yield 0.4 g, 17%).

EXAMPLE 62

Preparation of racemic(2'S,3S)-6-chloro-2'-[5-chloro-2-(2-hydroxycarbonyl-1-methyl-ethoxy)-phenyl]-4'-(5-fluoro-2-methyl-phenyl)-1',3'-dihydrospiro[3H-indole-3,3'-pyridine]-2,6'(1H)-dione

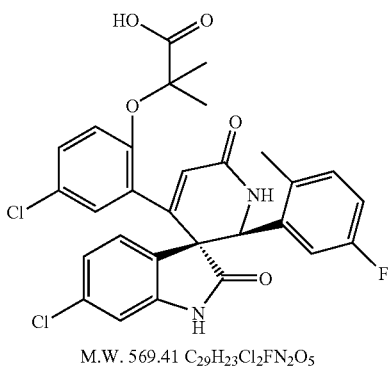

M.W. 569.41 C$_{29}$H$_{23}$Cl$_2$FN$_2$O$_5$

To a solution of racemic(2'S,3S,4'R,5'R)-4'-[2-(1-tert-butoxycarbonyl-1-methyl-ethoxy)-5-chloro-phenyl]-5',6-dichloro-2'-(5-fluoro-2-methyl-phenyl)spiro[3H-indole-3,3'-piperidine]-2,6'(1H)-dione (0.4 g, 0.6 mmol) in toluene (20 mL) was added 1,8-diazabicyclo[5.4.0]-undec-7-ene (DBU, Aldrich) (1.8 mL, 12 mmol). The reaction mixture was heated and stirred at 120° C. for 4 h. After cooled to room temperature, the mixture was concentrated. The residue was partitioned between water solution and ethyl acetate. The aqueous layer was extracted with ethyl acetate. The combined extracts were washed with water, brine, then dried over Na$_2$SO$_4$ and concentrated. The residue was purified by chromatography (EtOAc:CH$_2$Cl$_2$=1; 19, 1:9) The product was dissolved in dichloromethane (5 mL) and trifluoroactic acid (1 mL) was added. After the reaction mixture was stirred at room temperature for 20 h, the mixture was concentrated, and the residue was triturated with ethyl ether, hexanes to give racemic(2'S,3S)-6-chloro-2'-[5-chloro-2-(2-hydroxycarbonyl-1-methyl-ethoxy)-phenyl]-4'-(5-fluoro-2-methyl-phenyl)-1',3'-dihydrospiro[3H-indole-3,3'-pyridine]-2,6'(1H)-dione as an off-white solid (Yield 40 mg, 12%).

MS (ES$^+$) m/z Calcd C$_{29}$H$_{23}$Cl$_2$FN$_2$O$_5$+H [(M+H)$^+$]: 569.1041. Found: 569.1044

EXAMPLE 63

In Vitro Activity Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.). Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycocyanin (APC).

Test is performed in black flat-bottom 384-well plates (Costar) in a total volume of 40 uL containing:90 nM biotinylate peptide, 160 ng/ml GST-MDM2, 20 nM streptavidin-APC (PerkinElmerWallac), 2 nM Eu-labeled anti-GST-antibody (PerkinElmerWallac), 0.2% bovine serum albumin (BSA), 1 mM dithiothreitol (DTT) and 20 mM Tris-borate saline (TBS) buffer as follows: Add 10 uL of GST-MDM2 (640 ng/ml working solution) in reaction buffer to each well. Add 10 uL diluted compounds (1:5 dilution in reaction buffer) to each well, mix by shaking. Add 20 uL biotinylated p53 peptide (180 nM working solution) in reaction buffer to each well and mix on shaker. Incubate at 37° C. for 1 h. Add 20 uL streptavidin-APC and Eu-anti-GST antibody mixture (6 nM Eu-anti-GST and 60 nM streptavidin-APC working solution) in TBS buffer with 0.2% BSA, shake at room temperature for 30 minutes and read using a TRF-capable plate reader at 665 and 615 nm (Victor 5, Perkin ElmerWallac). If not specified, the reagents were purchased from Sigma Chemical Co.

IC$_{50}$'s showing the biological activity of this invention exhibit activities less than about 10 uM.

Representative values are, for example:

| Example | IC$_{50}$ (μM, 0.02% BSA) |
|---------|---------------------------|
| 6       | 0.066                     |
| 12      | 0.273                     |
| 16      | 0.482                     |
| 32      | 5.299                     |
| 40      | 6.415                     |

What is claimed:
1. A compound of the formula

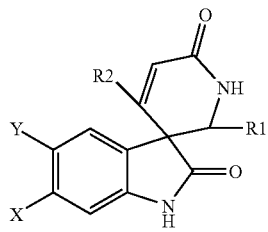

I wherein
X is selected from the group consisting of hydrogen, halogen, cyano, nitro, ethynyl, cyclopropyl, methyl, ethyl, isopropyl, methoxy and vinyl,
Y is hydrogen, hydroxyl, or fluorine,
R$_1$ is selected from the group consisting of lower alkenyl, substituted lower alkenyl, aryl, substituted aryl, heteroaryl, substituted heteroaryl, cycloalkenyl and substituted cycloalkenyl and
R$_2$ is selected from the group consisting of aryl, substituted aryl, heteroaryl, substituted heteroaryl, heterocycle, substituted heterocycle, cycloalkenyl and substituted cycloalkenyl or a pharmaceutically acceptable salt or ester thereof.

2. The compound of claim 1 having the formula

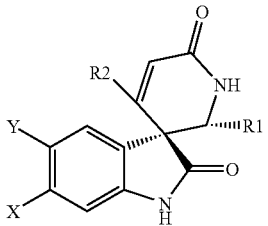

II wherein
X is selected from the group consisting of hydrogen, halogen, cyano, nitro, ethynyl, cyclopropyl, methyl, ethyl, isopropyl, methoxy, and vinyl,
Y is hydrogen, hydroxyl, or fluorine,
R$_1$ is selected from the group consisting of lower alkenyl, substituted lower alkenyl, aryl, substituted aryl, heteroaryl, substituted heteroaryl, cycloalkenyl and substituted cycloalkenyl and
R$_2$ is selected from the group consisting of aryl, substituted aryl, heteroaryl, substituted heteroaryl, heterocycle, substituted heterocycle, cycloalkenyl and substituted cycloalkenyl or a pharmaceutically acceptable salt or ester thereof.

3. The compound of claim 2 wherein
X is Cl, F or Br
Y is hydrogen,
R$_2$ is a substituted phenyl or substituted heteroaryl with the substituted phenyl or substituted heteroaryl selected from group consisting of:

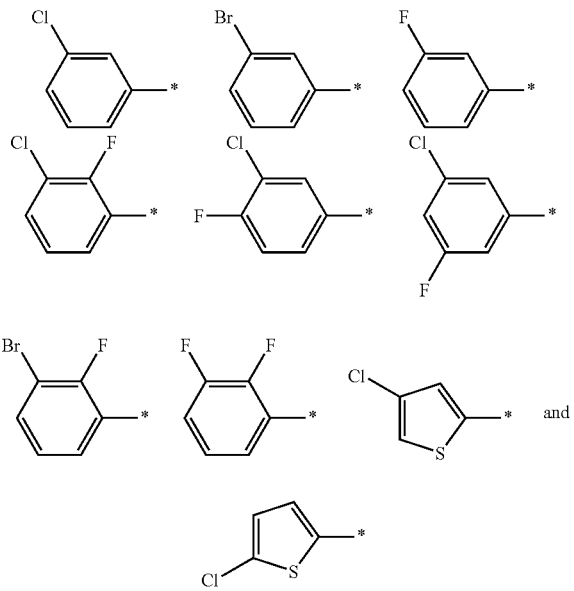

and

R$_1$ is selected from the group consisting of lower alkenyl, substituted lower alkenyl, aryl, substituted aryl, heteroaryl, substituted heteroaryl, cycloalkenyl and substituted cycloalkenyl or a pharmaceutically acceptable salt or ester thereof.

4. A compound of claim 1 selected from the group consisting of
racemic(2'R,3R)-6-chloro-4'-(3-chloro-phenyl)-2'-(5-fluoro-2-methyl-phenyl)-1',3'-dihydrospiro[3H-indole-3,3'(2'H)-pyridine]-2,6'(1H)-dione;
chiral(2'R,3R)-6-chloro-4'-(3-chloro-phenyl)-2'-(5-fluoro-2-methyl-phenyl)-1',3'-dihydrospiro[3H-indole-3,3'(2'H)-pyridine]-2,6'(1H)-dione;
racemic(2'R,3R)-6-chloro-4'-(3-chloro-phenyl)-2'-(5-fluoro-2-methyl-phenyl)-5-hydroxy-1',3'-dihydrospiro[3H-indole-3,3'(2'H)-pyridine]-2,6'(1H)-dione;
racemic(2'R,3R)-6-chloro-4'-(3-chloro-phenyl)-2'-[5-chloro-2-(tetrahydro-pyran-4-yloxy)-phenyl]-1',3'-dihydrospiro[3H-indole-3,3'-pyridine]-2,6'(1H)-dione;
racemic(2'R,3R)-6-chloro-2'-[5-chloro-2-(tetrahydro-pyran-4-yloxy)-phenyl]-4'-(3-fluoro-phenyl)-1',3'-dihydrospiro[3H-indole-3,3'-pyridine]-2,6'(1H)-dione;
racemic(2'R,3R)-6-chloro-2'-[5-chloro-2-(2-hydroxy-ethoxy)-phenyl]-4'-(5-fluoro-2-methyl-phenyl)-1',3'-dihydrospiro[3H-indole-3,3'-pyridine]-2,6'(1H)-dione;
racemic(2'R,3R)-6-chloro-4'-(3-chloro-phenyl)-2'-isopropenyl-1',3'-dihydrospiro[3H-indole-3,3'-pyridine]-2,6'(1H)-dione;
racemic(2'R,3R)-6-chloro-4'-(3-chloro-phenyl)-5-fluoro-2'-(5-fluoro-2-methyl-phenyl)-1',3'-dihydrospiro[3H-indole-3,3'(2'H)-pyridine]-2,6'(1H)-dione;
racemic(2'R,3R)-6-chloro-2'-(5-fluoro-2-methyl-phenyl)-4'-(furan-3-yl)-1',3'-dihydrospiro[3H-indole-3,3'(2'H)-pyridine]-2,6'(1H)-dione and racemic(2'R,3R)-6-chloro-2'-(5-fluoro-2-methyl-phenyl)-4'-(thiophen-3-yl)-1',3'-dihydrospiro[3H-indole-3,3'(2'H)-pyridine]-2,6'(1H)-dione.

5. A compound of claim 1 selected from the group consisting of racemic(2'R,3R)-6-chloro-2'-(5-fluoro-2-methyl-phenyl)-4'-(pyridin-3-yl)-1',3'-dihydrospiro[3H-indole-3,3'(2'H)-pyridine]-2,6'(1H)-dione;

racemic(2'R,3R)-6-chloro-4'-(3-chloro-phenyl)-2'-[5-iodo-2-(tetrahydro-pyran-4-yloxy)-phenyl]-1',3'-dihydrospiro[3H-indole-3,3'-pyridine]-2,6'(1H)-dione;

racemic(2'R,3R)-6-chloro-4'-(3-chloro-phenyl)-2'-[5-ethynyl-2-(tetrahydro-pyran-4-yloxy)-phenyl]-1',3'-dihydrospiro[3H-indole-3,3'-pyridine]-2,6'(1H)-dione;

racemic(2'S,3R)-6-chloro-4'-(3-chloro-phenyl)-2'-[5-ethynyl-2-(tetrahydro-pyran-4-yloxy)-phenyl]-1',3'-dihydrospiro[3H-indole-3,3'-pyridine]-2,6'(1H)-dione;

racemic(2'R,3R)-6-chloro-4'-(5-chloro-furan-2-ylmethylene)-2'-(5-fluoro-2-methyl-phenyl)-1',3'-dihydrospiro[3H-indole-3,3'(2'H)-pyridine]-2,6'(1H)-dione;

racemic(2'R,3R)-6-chloro-4'-(cyclopent-1-enyl)-2'-(5-fluoro-2-methyl-phenyl)-1',3'-dihydrospiro[3H-indole-3,3'(2'H)-pyridine]-2,6'(1H)-dione and racemic(2'S,3S)-6-chloro-2'-[5-chloro-2-(2-hydroxycarbonyl-1-methyl-ethoxy)-phenyl]-4'-(5-fluoro-2-methyl-phenyl)-1',3'-dihydrospiro[3H-indole-3,3'-pyridine]-2,6'(1H)-dione.

6. A pharmaceutical composition comprising a compound of the formula

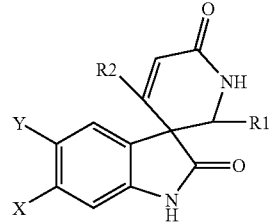

wherein

X is selected from the group consisting of hydrogen, halogen, cyano, nitro, ethynyl, cyclopropyl, methyl, ethyl, isopropyl, methoxy and vinyl, Y is hydrogen, hydroxyl, or fluorine, $R_1$ is selected from the group consisting of lower alkenyl, substituted lower alkenyl, aryl, substituted aryl, heteroaryl, substituted heteroaryl, cycloalkenyl and substituted cycloalkenyl and $R_2$ is selected from the group consisting of aryl, substituted aryl, heteroaryl, substituted heteroaryl, heterocycle, substituted heterocycle, cycloalkenyl and substituted cycloalkenyl or a pharmaceutically acceptable salt or ester thereof together with a pharmaceutically acceptable excipient or carrier.

* * * * *